(12) United States Patent
Feldman

(10) Patent No.: US 10,856,070 B2
(45) Date of Patent: Dec. 1, 2020

(54) THROAT MICROPHONE SYSTEM AND METHOD

(71) Applicant: VocoLabs, Inc., Skokie, IL (US)

(72) Inventor: Frederick M. Feldman, Skokie, IL (US)

(73) Assignee: VocoLabs, Inc., Skokie, IL (US)

( * ) Notice: Subject to any disclaimer, the term of this patent is extended or adjusted under 35 U.S.C. 154(b) by 0 days.

(21) Appl. No.: 16/657,508

(22) Filed: Oct. 18, 2019

(65) Prior Publication Data

US 2020/0128317 A1 Apr. 23, 2020

Related U.S. Application Data

(60) Provisional application No. 62/747,812, filed on Oct. 19, 2018.

(51) Int. Cl.
*H04R 1/14* (2006.01)
*H04R 19/04* (2006.01)
(Continued)

(52) U.S. Cl.
CPC ............. *H04R 1/14* (2013.01); *A61B 5/0488* (2013.01); *H04R 1/04* (2013.01); *H04R 1/083* (2013.01);
(Continued)

(58) Field of Classification Search
None
See application file for complete search history.

(56) References Cited

U.S. PATENT DOCUMENTS

| 7,283,850 B2 * | 10/2007 | Granovetter | G10L 15/20 455/570 |
| 7,574,357 B1 * | 8/2009 | Jorgensen | G10L 15/24 704/201 |

(Continued)

OTHER PUBLICATIONS

BeatboxMics "The Thumper TH100 Throat Microphone" Source: http://beatboxmics.com/#!/pages/th100, Aug. 23, 2018 (accessed from wayback machine web.archive.org indicating that the date of the document is Aug. 23, 2018). (p. 1).

(Continued)

*Primary Examiner* — Paul W Huber
(74) *Attorney, Agent, or Firm* — Lempia Summerfield Katz LLC

(57) ABSTRACT

A throat microphone system and method are disclosed. Certain people may have difficulty vocalizing, such as those suffering from neurodegenerative diseases. The throat microphone system includes a microphone unit that wirelessly communicates with an external device, such as a receiver unit in combination with a smartphone or a smartphone. The microphone unit includes a microphone and a wireless transceiver to wirelessly transmit sound data generated by the microphone. The smartphone processes the sound data in order to increase the intelligibility and/or the volume. Further, the microphone unit may attach to the neck of the wearer and may encircle the neck less than the entire perimeter of the neck. In this way, the microphone unit may be easily removed in the event the wearer is in distress. Moreover, the throat microphone system may include a non-audio sensor, such as a vibration sensor or an electromyograph sensor, in order to determine whether the wearer is voicing speech.

22 Claims, 22 Drawing Sheets

(51) Int. Cl.
*H04R 1/04* (2006.01)
*H04R 3/00* (2006.01)
*A61B 5/0488* (2006.01)
*H04R 1/08* (2006.01)

(52) U.S. Cl.
CPC ............... *H04R 3/00* (2013.01); *H04R 19/04* (2013.01); *H04R 2201/003* (2013.01); *H04R 2420/07* (2013.01)

(56) References Cited

U.S. PATENT DOCUMENTS

| | | | | |
|---|---|---|---|---|
| 2002/0183014 | A1* | 12/2002 | Takeda | H04R 1/14 455/73 |
| 2005/0196007 | A1* | 9/2005 | Yueh | H04M 1/6066 381/364 |
| 2013/0297301 | A1* | 11/2013 | Alberth, Jr. | H04M 1/7253 704/226 |
| 2015/0010172 | A1* | 1/2015 | Chen | H04R 1/14 381/151 |
| 2015/0104044 | A1* | 4/2015 | Lee | H04R 1/46 381/120 |
| 2015/0179189 | A1* | 6/2015 | Dadu | G10L 15/24 704/275 |
| 2015/0325249 | A1* | 11/2015 | Russell | G10L 21/02 381/122 |
| 2016/0037247 | A1* | 2/2016 | Sun | H04R 1/08 381/70 |
| 2016/0302003 | A1* | 10/2016 | Rahman | H04R 1/46 |
| 2016/0366513 | A1* | 12/2016 | Zhao | A61B 5/6822 |

OTHER PUBLICATIONS

BeatboxMics. Source: http://beatboxmics.com/, Sep. 23, 2018 (accessed from wayback machine web.archive.org indicating that the date of the document is Sep. 23, 2018). (pp. 1-2).

Feldman, Freddie "The Thumper TH100—Throat Microphone" Kickstarter. Source: https://www.kickstarter.com/projects/vocomotion/the-thumper-th100-throat-microphone, Aug. 20, 2013 (accessed from wayback machine web.archive.org indicating that the date of the document is Aug. 20, 2013). (pp. 1-4).

Universal Audio "Audio Compression Basics" Source: https://www.uaudio.com/blog/audio-compression-basics/, Aug. 26, 2017 (accessed from wayback machine web.archive.org indicating that the date of the document is Aug. 26, 2017). (pp. 1-9).

J. Ramirez, J. M. Gorriz and J. C. Segura, "Voice Activity Detection. Fundamentals and Speech Recognition System Robustness", Robust Speech Recognition and Understanding, ISBN: 978-3-902613-08-0, InTech, Available at: http://www.intechopen.com/books/robust_speech_recognition_and_understanding/voice_activity_detection_fundamentals_and_speech_recognition_system_robustness (pp. 1-11) (Jun. 2007).

* cited by examiner

US 10,856,070 B2

THROAT MICROPHONE SYSTEM AND METHOD

REFERENCE TO RELATED APPLICATION

The present application claims the priority benefit of U.S. Provisional Patent Application Ser. No. 62/747,812, the entirety of which is incorporated by reference herein.

FIELD OF THE INVENTION

The present application relates to a throat microphone system and method. More particularly, the present application relates to a throat microphone system and method that includes a wearable device (such as an adhesive wearable device) that wirelessly transmits audio data to an external electronic device for processing.

BACKGROUND

People living with neurodegenerative diseases such as Parkinson's, Amyotrophic Lateral Sclerosis (ALS), Multiple Sclerosis (MS), Muscular Dystrophy (MD), et al. encounter speech difficulties such as hypophonia. In this regard, people afflicted with those ailments have pronounced difficulty communicating with others.

BRIEF DESCRIPTION OF THE DRAWINGS

The accompanying drawings, which are incorporated in and constitute a part of this specification, illustrate various aspects of the invention and together with the description, serve to explain its principles. Wherever convenient, the same reference numbers will be used throughout the drawings to refer to the same or like elements.

DETAILED DESCRIPTION OF EMBODIMENTS

Overview

Figure 1A:
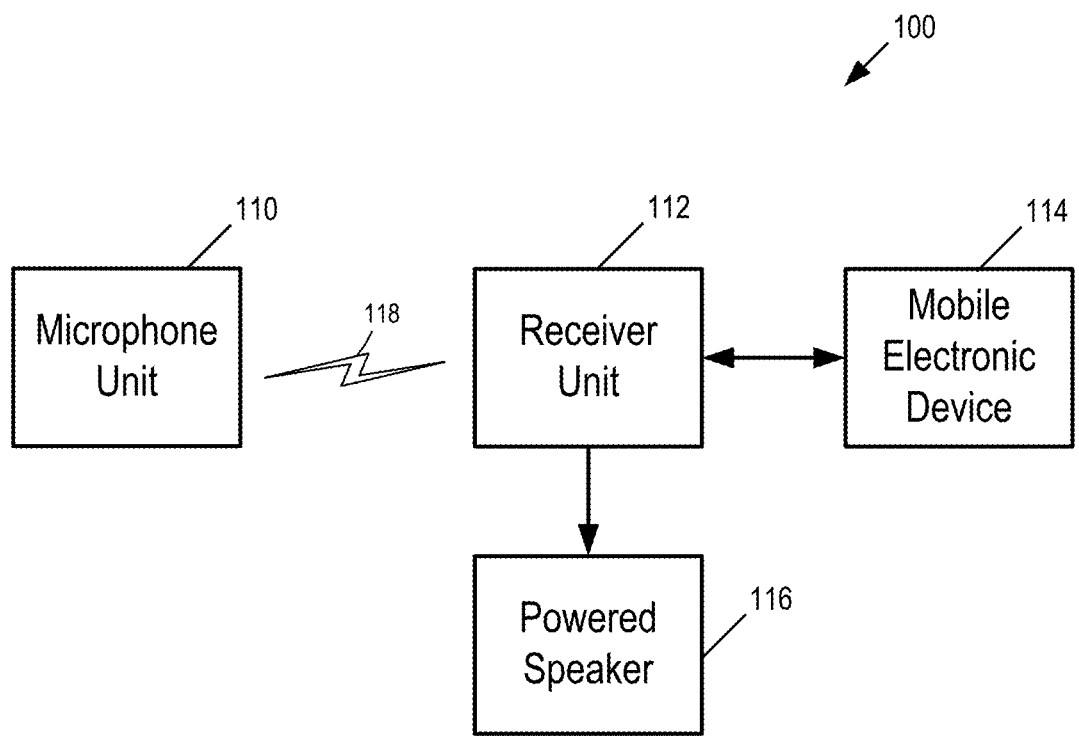
FIG. 1A is a first block diagram of a throat microphone system.

As discussed in the background, many have difficulty speaking, including those living with neurodegenerative diseases such as those afflicted with Parkinson's, ALS, MS, MD, throat cancer, spinal cord injuries, vocal cord paresis, and others afflicted with vocal dysphonia or hypophonia. The diminished speech intensity may reduce the sound output by 2-5 dB as compared to those unafflicted, resulting in a significant decrease in speech volume. Others may encounter shorter-term speech difficulties, such as those recovering from throat surgery (e.g., vocal node surgery). In either instance, people may have difficulty communicating verbally.

One option comprises an off-the-shelf boom-style microphone headset coupled with a small amplified speaker. However, this type of system does not: enhance the speech to increase the intelligibility of the amplified speech; provide for a way to use that speech digitally in any meaningful way (e.g., recording, streaming, and for voice command & control); or capture any metrics on their use or allow for the remote or even local adjustment of configuration & parameters. Further, using a boom-style headset microphone on a user, who may be connected to various forms of life support (e.g., ventilators, oxygen, or monitors) is simply an obstacle. In a crisis situation, these type of headsets are not easily removed if a patient requires immediate intervention. Wired microphones suffer from similar issues as they can be a hindrance to the user and medical staff.

In one implementation, the throat microphone system includes a microphone unit that wirelessly communicated with at least one external electronic device. In a first implementation, the throat microphone system includes the microphone unit, a receiver unit, and a mobile electronic device. The microphone unit, which includes a microphone (such as a MEMS microphone to generate sound data) and a transceiver, wirelessly communicates with the receiver unit, which includes a receiver. The receiver unit, in turn, communicates with the mobile electronic device via a wired connection (e.g., a port). One example of a mobile electronic device comprises a smartphone, which has multiple functionalities, such as processing functionality and communication functionality (e.g., Internet communication functionality, near-field communication functionality, far distance communication functionality, etc.). Any discussion herein with regard to a smartphone may likewise be applied to any other type of mobile electronic device, such as a tablet, a portable personal computer, or the like. As discussed in more detail below, the various functionalities of the smartphone may be used to: process the sound data generated by the microphone (e.g., increase the intelligibility of the sound data); and/or cause the processed sound data to be used (e.g., cause the processed sound data to be output on a speaker in order to increase the volume of the sound data; transmit the processed sound data to control a separate electronic device (e.g., the smartphone transmitting a command to an Amazon Alexa); transmit the processed sound data to a separate electronic device (e.g., transmit the processed sound data to another telephone for output); transmit the processed sound data to an external device (e.g., the smartphone transmitting the processed sound data to a cloud server for storage and/or analytics). As one example, the smartphone may transmit the processed sound data to an external electronic device, such as another smartphone, another landline telephone, a video-conference call, or the like. In this instance, transmitting the processed sound data to another electronic device may not require output via a powered speaker.

In this first implementation, due to issues of latency, the wireless near-field communication functionality of the smartphone is not used to communicate with the microphone unit; rather, the microphone unit communicates with the receiver unit using a near-field communication protocol that is unavailable in the smartphone and that has less latency than the wireless near-field communication functionality of the smartphone. Further, the smartphone may modify one or more parameters, which control the processing of the sound data, in order to improve at least one aspect of the sound data, such as intelligibility and/or volume.

In a second implementation, the throat microphone system includes the microphone unit and a mobile electronic device (without a separate receiver unit), in which the microphone unit wirelessly transmits the sound data directly to the mobile electronic device (e.g., the smartphone). In this implementation, the near-field communication protocol used by the microphone unit to communicate with the smartphone has sufficient latency for the application at hand. Further, similar to the first implementation, the smartphone may be used to process the sound data generated by the microphone and cause the processed sound data to be used.

Thus, in one implementation, the mobile electronic device (e.g., the smartphone) is configured to process the sound data. Processing of the sound data may include any one, any combination, or all of the following functions: amplification (e.g., increasing the volume of the sound); filtering (e.g., high pass filtering); voice activity detection (e.g., gating); auto-gain control (e.g., compression); consonant enhancement (e.g., using non-negative matrix factorization (NMF)); tone adjustment (e.g., equalization); and vocalization detection (e.g., compensating for whispering). The functions included in the processing may be controlled using one or more parameters, such as any one, any combination, or all of: the cut-off frequency for the filtering; the timing of the gating and/or the threshold of the gating for the auto-gain control; dynamic range for the auto-gain control; inputs for voice spectrum analysis and/or fast Fourier transforms for consonant enhancement; frequencies for enhancement or reduction for tone adjustment; whether to perform vocalization detection (e.g., parameter=1 to indicate always to perform vocalization detection; parameter=0 to indicate not to perform vocalization detection; parameter=2 to perform dynamic determination whether to perform vocalization detection); or inputs for power spectrum analysis for dynamic determination whether to perform vocalization detection; etc.

The parameter(s) for the processing may be configured in one of several ways. In one way, a profile, from a plurality of available profiles (that include the parameter(s)), may be selected. Thus, in one implementation, the profiles may adjust baseline settings of processing dependent on the condition of user (e.g., disease profile) and/or the environment. Each profile may comprise a collection of preset values for digital signal processing (DSP) parameters for use in the software (e.g., app) in the smartphone.

In one implementation, the plurality of profiles may be resident in the mobile electronic device (e.g., the smartphone). In practice, the clinician may input a selection via the mobile electronic device in order to select a particular profile, from the plurality of available profiles, that is best suited to the person wearing the microphone unit (the "wearer" or interchangeably the "speaker"). In this way, the clinician may configure an application executed by the mobile electronic device. In an alternate implementation, the plurality of profiles may be resident outside of the mobile electronic device, such as resident in a server (e.g., a cloud server). In practice, the clinician may access the server in order to download the selected particular profile for the wearer, thereby configuring the application executed the mobile electronic device. Alternatively, analysis, such as voice biomarker analysis, may be used by the mobile electronic device to select a profile, as discussed further below.

Various types of profiles are contemplated. In one implementation, the plurality of profiles may correlate to one or more aspects including: (1) aspects relating to the person (e.g., gender, affliction, age, nationality, etc.); and/or (2) environment (e.g., indoor usage, sports venue usage, theatre usage, medical diagnostic usage, confined space communications usage, etc.). For example, a first profile (which includes a first set of parameters) may be tailored for a female speaker (which may have a higher pitch voice) and a second profile (which includes a second set of parameters) may be tailored for a male speaker (which may have a lower pitch voice). As another example, the profiles may be correlated to the condition of the wearer. In one particular application, a Parkinson's disease profile may be tailored to a speaker afflicted with Parkinson's disease, a Multiple Sclerosis disease profile may be tailored to a speaker afflicted with Multiple Sclerosis, etc. For example, the Parkinson's disease profile may be configured to correct for the particularities affliction of Parkinson's disease. In particular, Parkinson's disease may result in tremors, so that tremor-type activity may be present in the diaphragm, resulting in the voice trembling in a certain manner. The mobile electronic device may access the profile in order to compensate for the vocal difficulties due to Parkinson's disease. Likewise, ALS disease may affect voicing speech in a particular way so that the ALS disease profile may compensate for such.

In one or some embodiments, the selected profile may modify one or more aspects in processing speech. As one example, the selected profile may alter one or more aspects associated compression, such as any one, any combination, or all of: threshold; knee; attack time; release time; compression ratio; or output gain. The threshold control may set the level at which the compression effect is engaged. In this regard, only when a level passes above the threshold will it be compressed. For example, if the threshold level is set at −10 dB, only signal peaks that extend above that level will be compressed. The rest of the time, no compression takes place. The knee may refer to how the compressor transitions between the non-compressed and compressed states of an audio signal running through it. In one embodiment, the compressor may offer one, or in some instances a switchable choice between both, a "soft knee" and a "hard knee" setting. Further, the compressor may allow control of the selection of any position between the two types of knees. Thus, a "soft knee" may allow for a smoother and more gradual compression than a "hard knee."

Attack time may refer to the time it takes for the signal to become fully compressed after exceeding the threshold level. Faster attack times may range between 20 and 800 µs, while slower attack times may range from 10 to 100 ms. This may be expressed as slopes in dB per second rather than in time. Fast attack times may create distortion by modifying inherently slow-moving low frequency waveforms.

Release time is the opposite of attack time. More specifically, release time is the time it takes for the signal to go from the compressed (e.g., attenuated) state back to the original non-compressed signal. Release times may be considerably longer than attack times, and may generally range anywhere from 40-60 ms to 2-5 seconds. Similar to attack times, release times may also be referenced as slopes in dB per second instead of times.

Compression ratio may specify the amount of attenuation to be applied to the signal. A wide range of ratios may be available (and may be selected based on the profile). For example, a ratio of 1:1 (one to one) is the lowest and it represents "unity gain", or in other words, no attenuation. Compression ratios may be expressed in decibels, so that a ratio of 1:2 indicates that a signal, which meets the threshold (or is determined to be voice) will be increased to 2 dB. The compression radio may be selected based on the profile accessed.

Thus, responsive to determining the person is suffering from Parkinson's disease (which results in tremors that cause the voice to fluctuate in volume erratically), the Parkinson's disease profile may be selected. In turn, the signal processing of the sound signal may use compression or automatic gain control in order to keep the volume more even (e.g., the signal processing may be more aggressive, such as more tightened, in order to clamp down on the dynamic range due to an anticipated larger fluctuation in volume). As another example, the signal processing may typically increase the volume of the speech (to amplify the voice) so that threshold of volume is set (e.g., if it signal strength is greater than a predetermined level, the volume downward is adjusted downward resulting in dynamic compression). For a disease that results in the volume fluctuating more severely, rapidly, or widely, the associated profile may restrict the range even further than is typically performed in the dynamic compression (e.g., in the compression of the dynamic range). Further, the selected profile may alter the attack time and/or the release time due to the effects of the disease (e.g., to attack faster and/or to release slower because there may be a more rapid change due to the Parkinson's disease). As still another example, the selected profile may lower the threshold (resulting in a change in the compression ratio) so that when the signal passes the threshold, the processing will reduce the volume in a manner tailored to the specific disease (e.g., by 1 dB for every dB over the threshold).

Likewise, for a disease that results in more a "breathy" sound and less voice, the profile may adjust the equalization to boost certain frequencies to enhance the vocalization of the speech. For example, articulation may be more difficult for certain afflictions. In this regard, the processor may enhance certain parts of the speech (such as emphasize the consonants of the sounds of the speech). Thus, the particular affliction of the wearer may be indicative of the quality of the speech generated by the wearer. In this regard, the profile, tailored to the particular affliction of the wearer, may tailor the processing to compensate for the respective quality of speech.

As still another example, multiple aspects may be used to factor into the profile, such as the disease, the gender, the age, the nationality (e.g., American speaker, British speaker, etc.), etc. In particular, a male Parkinson's profile may be tailored to a male speaker afflicted with Parkinson's disease and a female Multiple Sclerosis profile may be tailored to a female speaker afflicted with Multiple Sclerosis. Further, an American male Muscular Dystrophy profile may be tailored to an American male speaker afflicted with Muscular Dystrophy.

Further, in one implementation, the parameter(s) may be tailored to the speaker based on analysis of the processed sound data. The processed sound data may be stored in the smartphone and/or external to the smartphone (e.g., in the cloud) for future analysis. Based on the analysis, the parameter(s) may be modified. In particular, the application on the smartphone may log various metrics related to the usage of the microphone, such as, without limitation, start/stop time of usage, average speech intensity level, voice commands used, and others. The clinician may review these metrics, either locally on the smartphone or remotely logging into a server, in order to adjust the processing parameters.

Various metrics are contemplated including: how often the wearer is using the device (e.g., the frequency of use); how long the wearer is using the device (e.g., the total time in a day the wearer is using the device); the type of use (e.g., how often or how many commands are issued in a day; how many recordings generated); etc. For example, responsive to a clinician or the application server 140 identifying a pattern of use (e.g., the wearer is using the throat microphone system for ½ hour per day, mostly in the morning), the clinician and/or the server may recommend a change in usage (e.g., recommend increased usage and/or usage at different times of the day). In the instance of the server analyzing and recommending a change of usage, the server may compare the usage metrics for the wearer with predetermined usage metrics (e.g., usage metrics as doctor-recommended; usage metrics of similarly situated wearers). Thus, the software enables the collection of bio-informatics (such as compiling metrics) and parameter control (such as remote parameter control).

For example, a specific wearer may be assigned a certain profile based on the aspects relating to the specific wearer and/or the environment of the specific wearer. In one implementation, the analysis of the processed sound data may be performed locally. For example, the smartphone may analyze the processed sound data in order to determine whether to recommend modification of any one of the parameters currently being used. Alternatively, or in addition, the analysis of the processed sound data may be performed remotely. For example, a server, which accesses the processed sound data transmitted from the smartphone, may analyze the processed sound data in order to determine whether to recommend modification of any one of the parameters currently being used.

Based on analysis of the processed sound data, one or more of the parameters may be set or modified. In one implementation, the modification of the parameter(s) may be performed locally. For example, in practice, a clinician may modify the parameters via the user interface of the smartphone (e.g., such as via sliders and switches on the screen of the smartphone). Alternatively, or in addition, the modification of the parameter(s) may be performed remotely, such as via a server. In practice, a clinician may log into a server (such as a cloud server), determine whether to modify the parameter(s) (e.g., by the clinician analyzing the processed sound data himself or herself and/or by the clinician receiving a recommendation by the server to modify the parameter(s) based on the server's analysis of the processed sound data). The clinician may then confirm to the server the change(s) to the parameter(s). The change(s) to the parameter(s) may ultimately be sent to the smartphone, such as by pushing the change(s) to the smartphone or by waiting until the smartphone communicates with the server to receive the changes.

For example, responsive to analyzing the data generated by the throat microphone system, such as identifying that the volume is repeatedly being increased (or decreased), the amplification parameter may be adjusted (e.g., via the app or remotely) in order to modify the level of the volume output (e.g., increasing the volume output responsive to identifying a pattern of increasing the volume in the throat microphone system). Another example parameter comprises filtering. In practice, filtering may be adjusted responsive to analysis of the data. For example, the wearer may have a higher pitch voice. Responsive to identifying the pitch of the wearer as being higher, the filter may be adjusted to tailor the filter to someone with a higher pitch voice (e.g., modify the cutoff frequency of a high-pass filter). Conversely, responsive to identifying the pitch of the wearer as being lower, the filter may be adjusted to tailor the filter to someone with a lower pitch voice (e.g., modify the cutoff frequency of a high-pass filter).

In one implementation, the throat microphone system may be configured to voice un-voiced speech. Certain speech may be un-voiced, such as when someone is unable to speak above a whisper and/or unable to significantly move his/her vocal chords. Thus, in certain instances, the wearer may have difficulty voicing speech. The throat microphone system may first determine whether to perform the analysis whether to voice un-voiced speech, and if so, perform the analysis in order to determine whether to modify at least one aspect of the sound data (e.g., any one, any combination, or all of: pitch; rate; or volume).

There are multiple ways in which to trigger whether to perform the analysis whether to voice un-voiced speech. In one implementation, the trigger to perform vocalization detection may comprise a dynamic analysis to determine whether the wearer has un-voiced speech. The dynamic analysis may thus be indicative of whether the vocal chords of the wearer are moving (or an indication of the extent that the wearer's vocal chords are moving). This is distinct from other analyses of the sound data, including voice activity detection, which focuses on gating to determine whether the signal in the voice frequency range (e.g., at least a part of the audio range) is above a certain threshold for a least a certain period of time. In another implementation, a parameter may be pre-set, indicating that the analysis to determine whether to perform voicing of un-voiced speech is always performed (see above where parameter=1 to indicate always to perform vocalization detection).

Responsive to determining to perform the analysis whether there is unvoiced speech, the analysis of the sound data to determine whether there is unvoiced speech may be based on one or more inputs, including any one, any combination, or all of: the sound data itself (e.g., the text of the speech generated by a speech recognizer; the speech power spectrum data; etc.); a current status of the wearer (e.g., the heart-rate of the speaker); the position of the speaker (e.g., lying down or sitting up); etc.

Thus, in one implementation, the analysis may comprise identifying text in the sound data and performing one or more actions based on the identified text. In a first specific implementation, responsive to identifying one or more words in the sound data, the software may modify the sound data in one or more aspects. For example, responsive to vocalization detection (e.g., based on a parameter indicative of always performing vocalization detection or based on dynamic determination of vocalization detection), the software in the smartphone may identify one or more words, such as a single word (e.g., "what") or a sequence of words in the sound data.

As one example, responsive to identifying predetermined word(s) and/or a predetermined phrase (e.g., a set of words arranged in a predetermined order), a vocoder (or other type of human voice synthesizer) may adjust the pitch of the carrier frequency (e.g., the sine wave) that is being vocoded. Alternatively, or in addition, the volume may be adjusted (either adjusting the volume upward or downward responsive to identifying unvoiced speech).

In particular, the vocoder may use a carrier sound (such as a sine wave of 1 KHz) and modulate the voice signal thereon. In order to reduce the tendency of vocoders to output robotic-like speech, the pitch of the carrier wave may be dynamically selected based on the content (e.g., the words) in the audio signal. Thus, the pitch of the carrier frequency may be modified based on the content of what is being said. For example, responsive to identifying that the voice data is indicative of a question (e.g., identifying "what" at the beginning of a phrase and/or identifying a set of words indicative of a question), the pitch for the carrier frequency may be increased when outputting the end of the phrase in order to provide an inflection indicative of a question. Thus, in certain languages and cultures, such as British or American English, the indication of a question comprises an increase in pitch at the end of the sentence. As discussed herein, the profile associated with the wearer may include an associated nationality. In this regard, the profile, which may include nationality, may provide an indication as to the ways in which to voice unvoiced speech. Alternatively, or in addition, the volume to output the sound data may be modified based on the detected word or words. For example, based on an identification of a word that indicates emphasis (e.g., "really" detected on its own without other words), the volume and/or pitch of the output sound may be modified.

Thus, in one implementation, the processing algorithm may first be configured with one or more aspects of the wearer (e.g., gender and/or age of the wearer), which may be used thereafter to set the pitch range and rate of speech. A machine learning engine may be fed one or more inputs, such as any one, any combination or all of: a stream of text from the speech recognizer; speech power spectrum data; and the heart-rate of the speaker. Based on the one or more inputs, the machine learning engine may anticipate the flow of sentences, and may modify any one, any combination or all of the pitch of the carrier signal, the volume, or the rate to create inflections in the speech output. In this way, the algorithm may modify the output of the sound data in order to voice speech that the wearer is unable to voice.

In a second specific implementation, responsive to identifying one or more key words, such as wake-up words and/or control words, the software may perform one or more actions separate from (or instead of) outputting the sound data to a speaker. Various external electronic devices, such as Alexa, and Siri, may be controlled via voice typically have a "wake word" that is used to notify the external electronic device that the following speech should be used as a command. Responsive to the software identifying the wake-up words, the software may transmit a command to the external electronic device in order to control the external electronic device. In this regard, the smartphone may stream pre-processed audio to voice-assistant services, such as Apple Siri, Amazon Echo, Google, etc. Alternatively, or in addition, the software may identify its own wake-up word (e.g., "Hey, Voco") and thereafter search for a command, such as a command word (e.g., "record", "email", etc.) in the sound data. In this regard, the software enables the wearer to issue commands to the throat microphone system vocally using a wake-up word and a command.

In one implementation, the software on the smartphone may perform customized wake-word detection for implementing voice commands. In particular, the smartphone may include a speech recognizer configured to detect the utterance of the wake word, with the speech recognizer being trained using individuals tailored to the specific wearer. As one example, the inputs to the engine to train the speech recognizer may generally comprise speech input via the microphone (of the microphone unit) of those suffering from ailments resulting in difficulty communicating with others. As a further example, the speech recognizer may be tailored based on the assigned profile. In particular, for a profile associated with communicating in a confined space, the speech recognizer may be selected based on an engine trained with speech emanating from a confined space (such as the microphone unit being used in the confined space). In another example, the speech recognizer may be selected based on an engine trained with speech emanating from someone with Muscular Dystrophy. In this regard, the assigned profile (e.g., profile associated with a particular affliction; profile generally associated with those suffering from ailments resulting in difficulty communicating with others; profile associated with medical diagnostic charting; profile associated with athletes; etc.) may be determinative as to the speech recognizer used.

As discussed above, the microphone unit may comprise a microphone and a wireless transceiver. In one implementation, the microphone unit is positioned on the throat of the wearer, with the microphone unit being affixed to the throat via an adhesive. Further, in one implementation, the microphone unit does not encircle the entire perimeter of the throat. Rather, in a first specific implementation, the microphone unit encircles less than ½ of the perimeter of the throat. In a second specific implementation, the microphone unit encircles less than ¼ of the perimeter of the throat. In one implementation, the microphone may be connected with the wireless transceiver via wiring, such as a flex ribbon cable (or other type of flexible cable), with the microphone being positioned toward the front of the throat (such as near the Adam's apple or vocal chords) and the wireless transceiver being positioned backward (such as below the ear of the wearer). Thus, the microphone unit may be less obtrusive in one of several ways including: (1) requiring less space on the neck so as not to impinge on breathing tubes or the like; (2) being easier to remove in case there is a need for quick removal.

Further, in one implementation, the microphone unit may consist of a single microphone. Alternatively, the microphone unit may comprise more than one microphone, such as two microphones, three microphones, etc. In one implementation, the multiple microphones may be positioned at different angles, with the sound data from the multiple microphones being used to process the sound data.

Thus, the throat microphone system may be used in a variety of contents. In one context, the throat microphone system may be used by a wearer with neurodegenerative diseases or those with speech difficulties. In another context, the throat microphone system may be used by a wearer in a confined space (e.g., the wearer is a motorcycle rider; the wearer is an athlete, such as a football quarterback). In still another context, the throat microphone system may be used by a wearer for medical diagnostic charting. For example, when a medical professional, such as a periodontist, uses charting software, the periodontist measures pockets in a patient's gums and can recite numbers or indications as to the state of the patient's gums. The periodontist may aurally state the dynamic analysis of different sections of the gums, thereby allowing the microphone unit to capture the vocal input, and transfer the vocal input to the smartphone for storage and/or transmission to an external server. In yet another context, the throat microphone system may be used by a wearer in a theater and other performance. As one example, a performer may use the microphone unit, being less obtrusive than a typical microphone. As another example, the performer may be a beatboxer, mimicking drum machines. In this instance, the processing of the sound data for the beatboxer may be modified, such as using a low-pass filter instead of a high-pass filter, in order to focus the frequency range from the vocal frequency range to the bass frequency range.

In one or some embodiments, at least a part of the system, such as one, some, or all of the microphone unit, the mobile electronic device, or the receiver unit, may assist in the capture and/or processing of voice biomarkers. Voice biomarkers (also known as vocal biomarkers) is a biological marker (or other medical sign) gleaned or deduced from a voice stream of a person. Voice biomarkers may detect certain diseases (such as Alzheimer's disease, Parkinson's disease, or coronary artery disease) and/or certain mental states (such as depression) than in other conventional ways.

The at least a part of the system (interchangeably termed a device), such as the microphone unit, the mobile electronic device, or the receiver unit, may be used in combination with voice biomarker analysis in one of several ways. In one way, the device may be used to capture the voice stream and to transmit the voice stream to another device (such as wireless transmit to a back-end server) in order for the another device to perform the voice biomarker analysis (e.g., analyze the voice stream in order to glean the voice biomarkers in order to diagnose disease or mental state). In another way, the device may be used to capture the voice stream and to perform the voice biomarker analysis locally.

In still another way, the device may be modified based on the voice biomarker analysis. In particular, the voice biomarker analysis may diagnose a certain disease or a certain mental condition. Responsive to the diagnosis, the device may be modified in one or more ways, such as modified in the processing of the input voice stream and/or modified in the output of the processed voice stream. For example, the device may modify its operation by assigning a profile tailored to the diagnosed disease or mental condition. As discussed above, the device may implement certain profiles, such as a Parkinson's disease profile, an Alzheimer's disease, etc. in order to tailor the processing of the input voice stream and/or the output. The profiles may be stored locally on the device, with the device selecting one profile from the plurality of profiles locally stored. Alternatively, the profile may be dynamically downloaded to the device. Thus, responsive to the voice biomarker analysis (either performed remotely at a back-end server or performed locally at the device), the device may be tailored based on the voice biomarker analysis (such as by selection of a Parkinson's disease profile responsive to voice biomarker analysis indicating Parkinson's disease).

The voice biomarker analysis may be performed in one of several ways. In one way, the person's voice stream (generated by the device) may be analyzed at one point in time. Alternatively, the person's voice stream (generated by the device) may be analyzed at multiple points in time (such as daily, weekly, monthly, etc.) in order to detect progression of the disease or the mental state.

Separate from (or in addition to) analyzing voice biomarkers for detecting disease or mental state, the analysis of the voice biomarkers may be used for identification. For example, in the event that multiple people use the same microphone unit, analysis of the voice biomarkers may identify the specific user and then use the specific profile associated with the identified person. In particular, a shared microphone unit may be used in a nursing home, with the microphone unit storing the profiles (or configured to access remotely stored profiles) for each of the people that may use the microphone. In practice, the microphone unit may identify the person (using the voice biomarkers) and thereafter access and use the identified person's corresponding profile. Alternatively, or in addition, identification, based on analysis of the voice biomarkers, may be used for authentication (e.g., instead of or in addition to passwords for access to a device, an account, or a profile).

In one or some embodiments, detection of voice emanating from the person (e.g., the patient) wearing the microphone may be based on data generated by non-audio sensor, such as a vibration sensor, positioned or placed on the body of the person. By way of background, the microphone in a microphone unit may be configured to generate audio data. The microphone unit may seek to only process audio data that is generated by vocal sounds of the person (as opposed to audio data that is generated by other sounds, such as other speakers, other external noises, or the like). Typically, one may examine the audio data itself in order to determine whether the audio data (represented as a voice stream) includes voice on it. For example, a voice activity detector (alternatively known as voice activity detection) may analyze the voice stream, as discussed in more detail below. As another example, the audio data may be compared to a threshold in order to determine whether voice is present in the stream (e.g., if the amplitude is higher than a threshold, it is determined that voice is present). However, relying simply on examining the audio data may result in instances where sound, generated other than by the person wearing or proximate to the microphone unit, triggers processing of the audio data.

Thus, in one or some embodiments, another sensor may be positioned on or in fixed relation to the person and configured to sense at least one aspect associated with the person in order for the sensor to generate non-audio data, which is indicative of the person speaking. For example, when a person speaks, the person may have vibrations that emanate in one or more parts of the body, such as in the throat and/or in the ear. As another example, when a person speaks, the person may have attendant muscle movements, such as the throat muscles moves responsive to the person forming the sounds. In this regard, one or more sensors may be used to generate data (e.g., non-audio data) to sense at least one aspect associated with the person that is indicative of the person speaking.

In one or some embodiments, the sensor is positioned on or in the body of the person and comprises a vibration sensor configured to sense vibration and generate vibration data. The sensor may be positioned in or on any one, any combination, or all of: on the throat (e.g., on or proximate to the hyoid bone; on or proximate to the thyroid cartilage; on or proximate to the cricoid cartilage; on or proximate to the hypoglossasal nerve; on or proximate to the sternocleidomastoideus; on or proximate to the omohyoideus; on or proximate to the suprahyoid muscles; or on or proximate to the infrayoid muscles); on a part of the face (e.g., on or proximate to the cheek; on or proximate the mouth); on a part of the ear (e.g., at least partly within the ear canal). As one example, the vibration sensor may be placed on at least a part of the throat in order to sense vibrations caused by speech from the person. As another example, the vibration sensor may be placed on or in the ear canal, thereby sensing vibrations in the ear canal (e.g., through bone conduction, voice sounds emanating from the throat causes vibrations in the person's skull and in turn the ear bones).

Alternatively, or in addition, the sensor is positioned on or in the body of the person and comprises a sensor configured to sense muscle movement in order to generate muscle movement data. As one example, an electromyograph sensor may be used. Specifically, the electromyograph sensor may be configured to detect movement of the nerves stimulating/flexing in the throat, thereby generating electromyograph data (e.g., an electromyogram) indicative of recording of the electrical activity of muscle tissue (such as in one of the throat muscles). Thus, the microphone unit may use electromyography as an electrodiagnostic medicine technique for recording the electrical activity produced by skeletal muscles, and in turn used to determining whether the person is generating speech. Alternatively, the sensor may comprise a contact microphone, accelerometer, or other type of vibrational sensor mounted against a part of the body of the wearer (such as against the neck of the wearer).

In one embodiment, a voice detector may analyze the non-audio data, generated by the sensor, in order to determine whether the non-audio data is indicative of the person speaking. For example, when using a vibration sensor, the voice detector may compare the vibration data with a vibration threshold. Responsive to determining that the amplitude of the vibration data is greater than or equal to the vibration threshold (e.g., the vibration data is of sufficient magnitude to indicate that the person is speaking), the voice detector may determine that the person is speaking. Conversely, responsive to determining that the amplitude of the vibration data is less than the vibration threshold, the voice detector may determine that the person is not speaking. As another example, when using an electromyograph sensor, the voice detector may compare the electromyograph data with an electromyograph threshold. Responsive to determining that the amplitude of the electromyograph data is greater than or equal to the electromyograph threshold (e.g., the electromyograph data is of sufficient magnitude to indicate that the person is making muscle movements consistent with one who is speaking), the voice detector may determine that the person is speaking. Conversely, responsive to determining that the amplitude of the electromyograph data is less than the electromyograph threshold, the voice detector may determine that the person is not speaking.

Thus, in one embodiment, the voice detector may solely analyze the non-audio data in order to determine whether the non-audio data is indicative of the person speaking. Alternatively, the voice detector may analyze the non-audio data in combination with other audio data in order to determine whether the person is speaking. For example, the voice detector may use a Voice Activity Detector (interchangeably referred to as Voice Activity Detection) along with analyzing the non-audio data in order to determine whether person is speaking.

As discussed above, the non-audio data sensor and the microphone may be positioned in various orientations relative to one another. In one embodiment, the non-audio data sensor and the microphone are in the same housing and positioned on the same part of the body of the person. For example, the vibration sensor or the electromyograph sensor may be positioned in the same housing as the microphone, with the housing configured for attachment on the throat of the person. In another embodiment, the non-audio data sensor and the microphone are in different housings and positioned in or on different parts of the body of the person. As one example, the vibration sensor may be housed in an earpiece for attachment in or on the ear (e.g., a bone-conduction microphone sensor placed in or near the ear canal) while the microphone may be positioned for attachment close to the mouth or on the throat. As another example, the microphone may be positioned for attachment on the body of the person near the mouth and the vibration sensor positioned for attachment on the throat. In this way, the vibration sensor may be positioned on the body of the person below the microphone.

In addition, the voice detector, analyzing the non-audio data to determine whether the person is speaking, may be used for various purposes. As one example, the voice detector may help with reducing noise transmission and feedback. In particular, with regard to feedback, processing of the audio data may be triggered only responsive to detecting that the person (e.g., the wearer) is speaking. For example, the processor analyzing one or both of the non-audio data or the voice activity detector may employ hysteresis functions, machine learning, or other artificial intelligence algorithms in order to assemble the proper vibrational profile to detect when the wearer is actually speaking.

Further, the voice detector may be used in a variety of contexts. For example, the voice detector may be used with the throat microphone, as discussed above. As another example, the voice detector may be positioned on a part of various types of headsets. In particular, the voice detector may be integrated into a mobile phone headset for use with a mobile phone. In this way, the voice detector may detect the person's speech, even in a noisy area, such as a restaurant. Alternatively, the voice detector may be integrated in a headset for a stage manager of a show, in other types of headborne microphones, or other types of boom headsets worn for communication. For example, the non-audio data sensor may be integrated into the headset such that when worn, at least a part of the headset (which houses the non-audio data sensor) presses against one or more parts of the person, such as around the ear of the person and/or against at least a part of the neck.

The voice detector may likewise be integrated in a helmet, such as a motorcyclist's helmet (e.g., the non-audio data sensor, such as the vibration sensor or the electromyograph sensor, may be positioned across the strap or the hard plastic piece that contacts the throat of the motorcyclist).

Referring to the figures, FIG. 1A is a first block diagram of a throat microphone system 100. Throat microphone system 100 includes microphone unit 110, receiver unit 112, mobile electronic device 114, and powered speaker 116. Microphone unit 110 communicates wirelessly 118 with receiver unit 112. As discussed further with regard to FIG. 5, receiver unit 112 is connected (such as physically connected) to mobile electronic device so that receiver unit communicates with mobile electronic device via a wired connection.

Further, receiver unit 112 is configured to drive powered speaker 116 in order to generate the audio output of the processed sound data. Thus, in one implementation, the receiver unit 112 may include a headphone jack into which a plug (not shown) for the powered speaker 116 may be inserted. Alternatively, the powered speaker 116 may be driven by the mobile electronic device 114. In still an alternate implementation, the powered speaker 116 is not included. In one example, a speaker on the mobile electronic device 114 (such as the speaker resident on the smartphone) may be used to output the processed sound data. In yet another example, the processed audio data is not output via a speaker, as discussed above.

In certain instances, the near-field communication functionality of the mobile electronic device 114 may be insufficient due to latency. In particular, wireless microphones, using a common transmission protocol such as Bluetooth that are resident in the smartphone, may introduce an unacceptable amount of latency into the transmission and reception of digital audio. In this regard, the receiver unit 112 communicates wirelessly with microphone unit 110 instead of the smartphone communicating wirelessly with microphone unit 110. Thus, in this instance, the receiver unit 112 includes near-field communication functionality in order to communicate with the microphone unit 110. Further, the mobile electronic device 114 does not use its near-field communication functionality in order to communicate with the microphone unit 110.

Figure 1B:
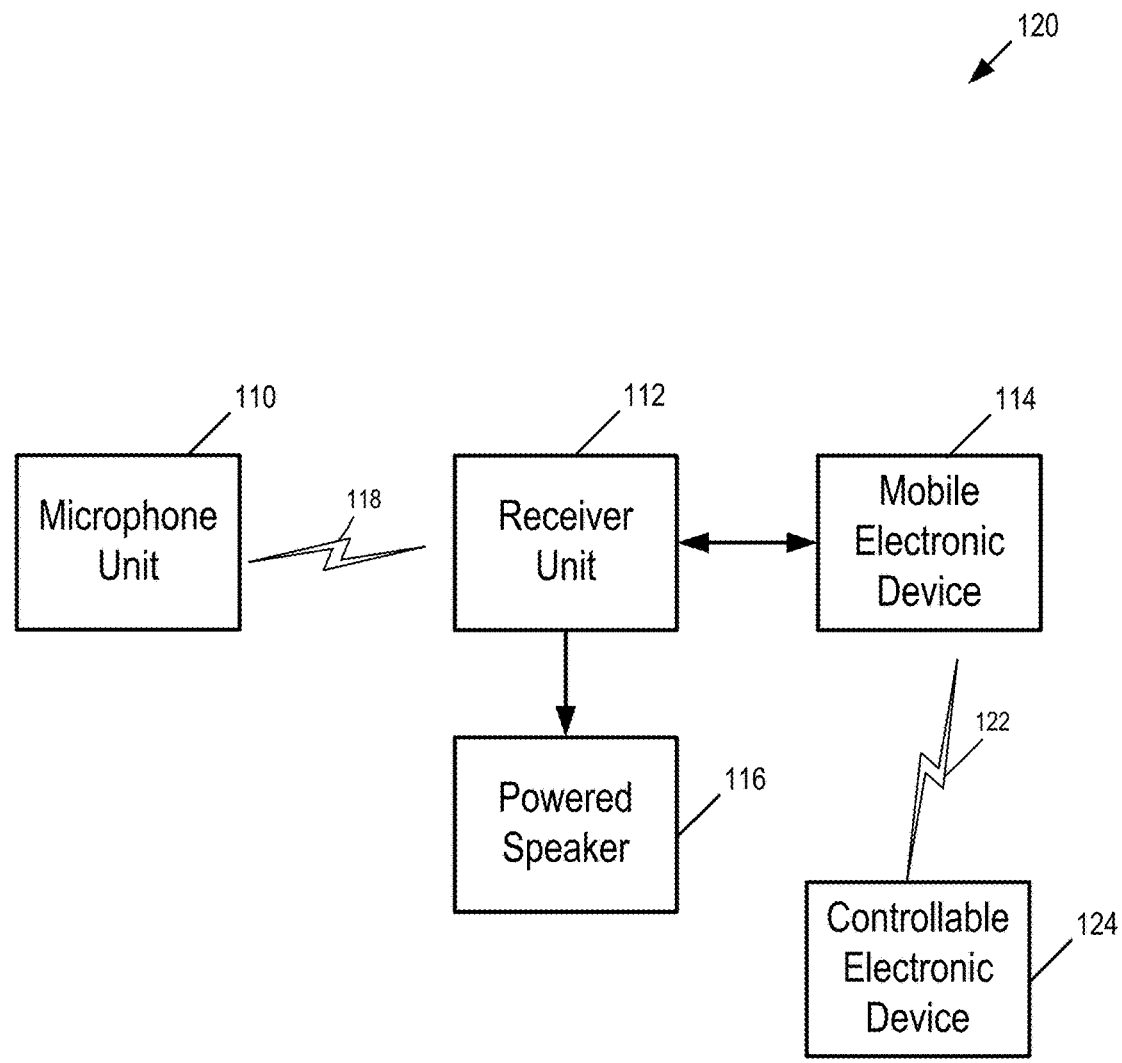
FIG. 1B is a second block diagram of a throat microphone system.

FIG. 1B is a second block diagram of a throat microphone system 120. FIG. 1B is similar to FIG. 1A with the addition of controllable electronic device 124. As discussed above, the mobile electronic device 114 (e.g., the smartphone) may send one or more commands to an external controllable electronic device 124, such as an Amazon Echo. Responsive to the mobile electronic device 114 determining that the sound data is directed to controlling an external electronic device (e.g., identifying a "wake-word" associated with the external electronic device), the mobile electronic device 114, may send via a wireless communication 122, a command to the controllable electronic device 124.

Figure 1C:
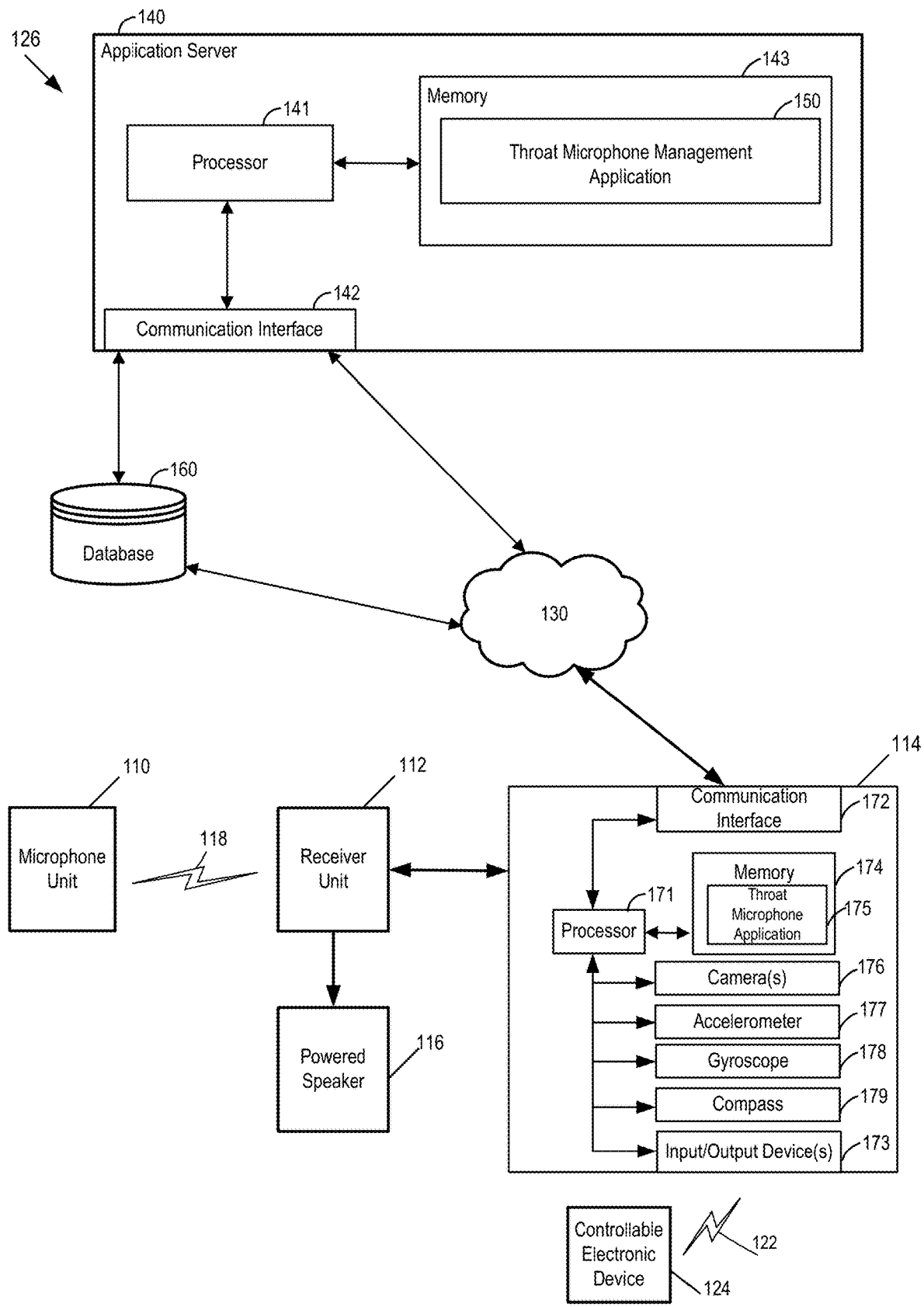
FIG. 1C is a block diagram of a system that includes the throat microphone system, such as illustrated in FIGS. 1A-B and 1D-E, communicating with application server.
Figure 1D:
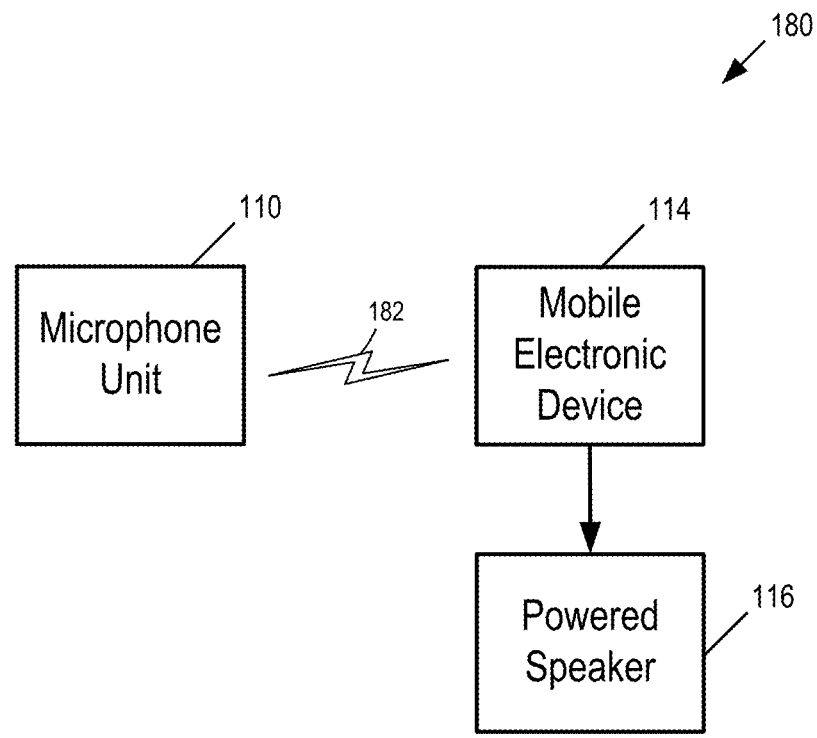
FIG. 1D is a third block diagram of a throat microphone system.

FIG. 1C is a block diagram of a system 126 that includes the throat microphone system, such as illustrated in FIGS. 1A-B and 1D, communicating with application server 140. As discussed above, the mobile electronic device 114 may communicate with one or more external electronic devices, such as application server 140 for managing the throat microphone system. The application server 140 is configured to include the hardware, software, firmware, and/or middleware for operating the throat microphone management application 150. Application server 140 is shown to include a processor 141, a memory 143, and a communication interface 142. The throat microphone management application 150 is described in terms of functionality to manage various stages of managing the throat microphone system, such as any one, any combination, or all of: initial configuration of one or more parameters of the throat microphone system; storing data (such as metrics) associated with the throat microphone system; analyzing the stored data; and reconfiguring the parameter(s) of the throat microphone system.

The throat microphone management application 150 may be a representation of software, hardware, firmware, and/or middleware configured to implement the management of any one, any combination, or all of the stages of the throat microphone system. The system 126 may further include a database 160 for storing data for use by the throat microphone management application 150. For example, metrics generated by the throat microphone system may be stored in database 160.

Figure 2:
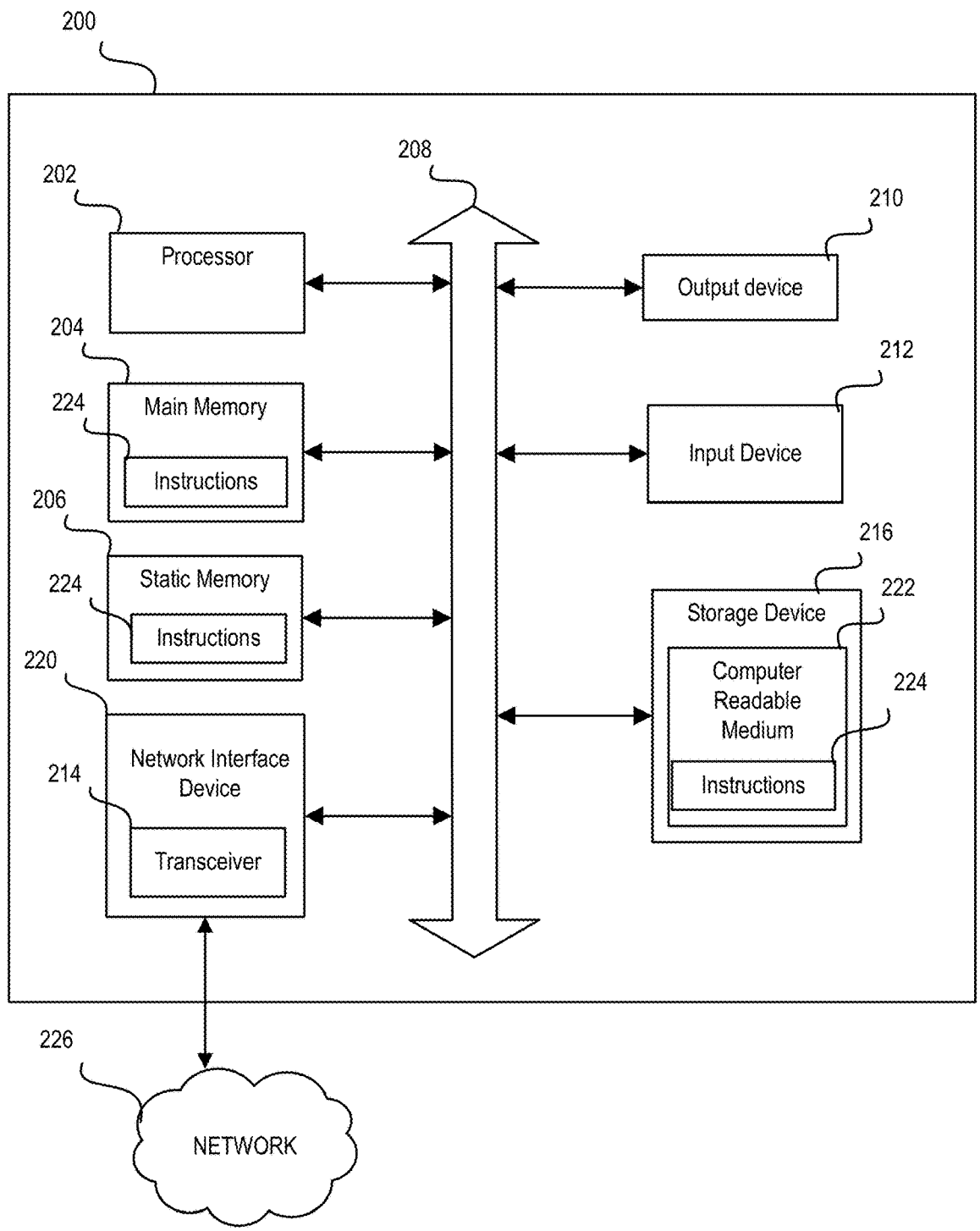
FIG. 2 is a general computer system, programmable to be a specific computer system, which may represent any of the computing devices referenced herein, such as the mobile electronic device (e.g., the smartphone) and the application server.

The application server 140 may communicate with the database 160 directly to access the data. Alternatively, the application server 140 may also communicate with the database 160 via network 130 (e.g., the Internet). Though FIG. 2 illustrates direct and indirect communication, in one implementation, only direct communication is used, in an alternate implementation, only indirect communication is used, and still in an alternate implementation, both direct and indirect communication is used.

The application server 140 may communicate with any number and type of communication devices via network 130. For example, application server 140 may communicate with throat microphone systems with one or more users. For example, FIG. 2 depicts communication with a single throat microphone system; however, communication with more than one throat microphone system is contemplated (e.g., such as communication with at least 10 throat microphone systems, with at least 100 throat microphone systems, or with at least 1,000 throat microphone systems). Thus, the depiction in FIG. 2 is merely for illustration purposes. Greater numbers of throat microphone systems are contemplated.

Mobile electronic device 114 shown in FIG. 1C may include well known computing systems, environments, and/or configurations that may be suitable for implementing features of the throat microphone application 175 such as, but are not limited to, smartphones, tablet computers, personal computers (PCs), server computers, handheld or laptop devices, multiprocessor systems, microprocessor-based systems, network PCs, or devices, and the like. FIG. 1C further shows that mobile electronic device 114 includes a processor 171, a memory 174 configured to store the instructions for operating throat microphone application 175 (the functionality being discussed further below), input/output device(s) 173 (such as touch sensitive displays, keyboards, or the like), and a communication interface 172 (which may include any one, any combination, or all of: near-field communication (e.g., Bluetooth); cellular communication; Internet communication). The memory 174, as part of the throat microphone application 175 or separately, may store one or more profiles, as discussed above. Throat microphone application 175 may be a representation of software, hardware, firmware, and/or middleware configured to implement functionality of the throat microphone system discussed herein.

Mobile electronic device 114 may include one or more sensors, such as camera(s) 176, accelerometer 177, gyroscope 178, and compass 179. As one example, data generated by accelerometer 177 may be used to determine whether the wearer is subject to tremors, and responsive to determining that the wearer is subject to tremors, adjust the audio parameters to counteract the tremors.

The various electronic devices depicted in FIG. 1C may be used in order to implement the functionality discussed herein. In this regard, mobile electronic device 114 may include one or more components of computer system 200 illustrated in FIG. 2.

FIG. 1D is a third block diagram of a throat microphone system 180. As discussed above, in one implementation, the microphone unit 110 communicates indirectly, via receiver unit 112, with mobile electronic device 114. Alternatively, the microphone unit 110 may communicate wirelessly 182 directly with mobile electronic device 114, such as illustrated in FIG. 1D. In this instance, the near-field communication (such as illustrated in communication interface 172) may be used to communication directedly with microphone unit 110. Further, the throat microphone system 180 may be applied to the implementations illustrated in FIGS. 1B-C, in which the throat microphone system 180 communicates with controllable electronic device 124, and communicates with application server 140.

Figure 1E:
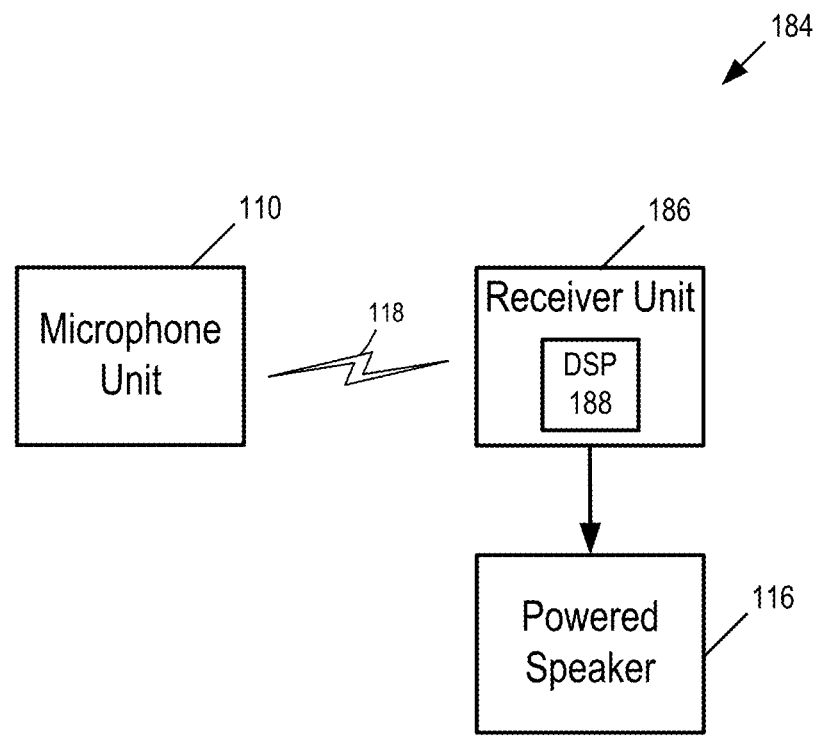
FIG. 1E is a fourth block diagram of a throat microphone system.

FIG. 1E is a fourth block diagram of a throat microphone system 184. As illustrated in FIG. 1E, throat microphone system 184 includes microphone unit 110 and receiver unit 186. Receiver unit 186 includes digital signal processor (DSP) 188, which may include the functionality that is performed by mobile electronic device 114 illustrated in FIGS. 1A-D and 6-7 (discussed below).

Figure 1F:
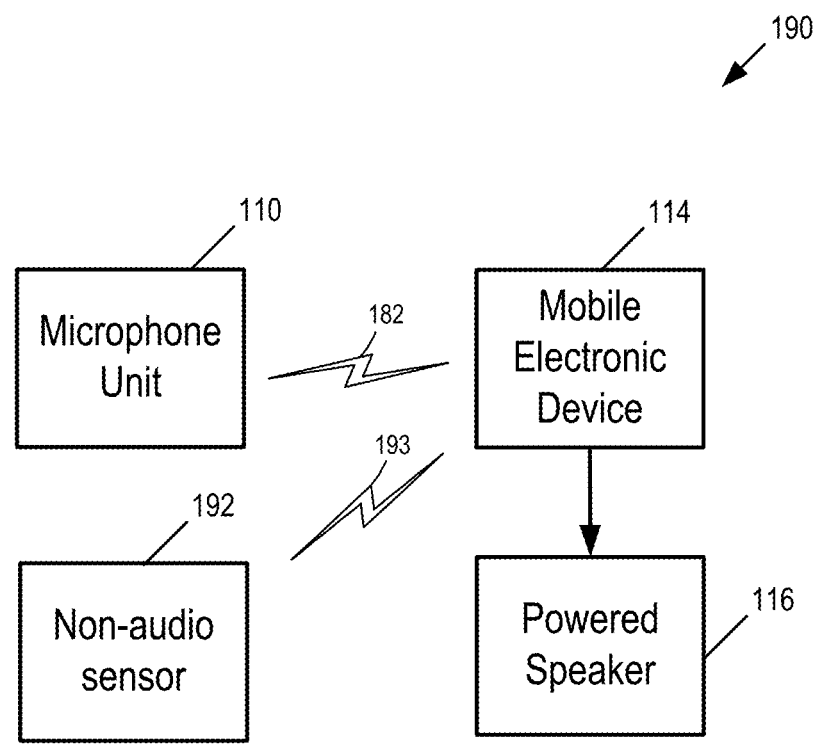
FIG. 1F is a fifth block diagram of a throat microphone system.
Figure 1G:
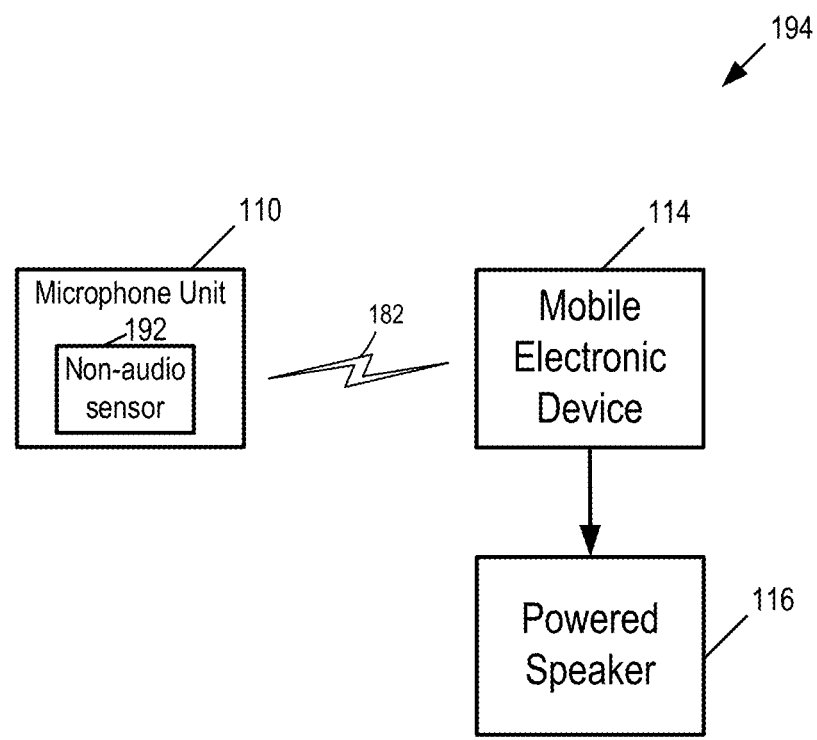
FIG. 1G is a sixth block diagram of a throat microphone system.

FIG. 1F is a fifth block diagram of a throat microphone system 190. As shown, FIG. 1F includes a non-audio sensor 192 configured to generate non-audio data. The non-audio sensor 192 may comprise a vibration sensor or an electromyograph sensor. In one or some embodiments, the non-audio sensor 192 is housed separately from the microphone unit 110. In such implementations, the non-audio sensor 192 may communicate separately with the mobile electronic device 114, such as wirelessly 193. Alternatively, the non-audio sensor 192 is housed within the microphone unit 110. In such implementations, the non-audio sensor 192 may communicate via 182. This is illustrated in FIG. 1G of throat microphone system 194.

FIG. 2 illustrates exemplary computer architecture for computer system 200. Computer system 200 includes a network interface 220 that allows communication with other computers via a network 226, where network 226 may be represented by network 130 in FIG. 1C. Network 226 may be any suitable network and may support any appropriate protocol suitable for communication to computer system 200. In an implementation, network 226 may support wireless communications. In another implementation, network 226 may support hard-wired communications, such as a telephone line or cable. In another implementation, network 226 may support the Ethernet IEEE (Institute of Electrical and Electronics Engineers) 802.3x specification. In another implementation, network 226 may be the Internet and may support IP (Internet Protocol). In another implementation, network 226 may be a LAN or a WAN. In another implementation, network 226 may be a hotspot service provider network. In another implementation, network 226 may be an intranet. In another implementation, network 226 may be a GPRS (General Packet Radio Service) network. In another implementation, network 226 may be any appropriate cellular data network or cell-based radio network technology. In another implementation, network 226 may be an IEEE 802.11 wireless network. In still another implementation, network 226 may be any suitable network or combination of networks. Although one network 226 is shown in FIG. 2, network 226 may be representative of any number of networks (of the same or different types) that may be utilized.

The computer system 200 may also include a processor 202, a main memory 204, a static memory 206, an output device 210 (e.g., a display or speaker), an input device 212, and a storage device 216, communicating via a bus 208.

Processor 202 represents a central processing unit of any type of architecture, such as a CISC (Complex Instruction Set Computing), RISC (Reduced Instruction Set Computing), VLIW (Very Long Instruction Word), or a hybrid architecture, although any appropriate processor may be used. Processor 202 executes instructions 224 stored on one or more of the main memory 204, static memory 206, or storage device 215. Processor 202 may also include portions of the computer system 200 that control the operation of the entire computer system 200. Processor 202 may also represent a controller that organizes data and program storage in memory and transfers data and other information between the various parts of the computer system 200.

Processor 202 is configured to receive input data and/or user commands through input device 212. Input device 212 may be a keyboard, mouse or other pointing device, trackball, scroll, button, touchpad, touch screen, keypad, microphone, speech recognition device, video recognition device, accelerometer, gyroscope, global positioning system (GPS) transceiver, or any other appropriate mechanism for the user to input data to computer system 200 and control operation of computer system 200 and/or operation of the throat microphone application 175. Input device 212 as illustrated in FIG. 2 may be representative of any number and type of input devices.

Processor 202 may also communicate with other computer systems via network 226 to receive instructions 224, where processor 202 may control the storage of such instructions 224 into any one or more of the main memory 204 (e.g., random access memory (RAM)), static memory 206 (e.g., read only memory (ROM)), or the storage device 216. Processor 202 may then read and execute instructions 224 from any one or more of the main memory 204, static memory 206, or storage device 216. The instructions 224 may also be stored onto any one or more of the main memory 204, static memory 206, or storage device 216 through other sources. The instructions 224 may correspond to, for example, instructions that throat microphone management application 150 or throat microphone application 175 illustrated in FIG. 1C, or represented in flow charts in FIGS. 6-7.

Although computer system 200 is represented in FIG. 2 as a single processor 202 and a single bus 208, the disclosed implementations applies equally to computer systems that may have multiple processors and to computer systems that may have multiple busses with some or all performing different functions in different ways.

Storage device 216 represents one or more mechanisms for storing data. For example, storage device 216 may include a computer readable medium 222 such as read-only memory (ROM), RAM, non-volatile storage media, optical storage media, flash memory devices, and/or other machine-readable media. In other implementations, any appropriate type of storage device may be used. Although only one storage device 216 is shown, multiple storage devices and multiple types of storage devices may be present. Further, although computer system 200 is drawn to contain the storage device 216, it may be distributed across other computer systems that are in communication with computer system 200, such as a server in communication with computer system 200. For example, when computer system 200 is representative of mobile electronic device 114, storage device 216 may be distributed across to application server 140 when mobile electronic device 114 is in communication with application server 140 during operation of the throat microphone management application 150 and/or throat microphone application 175.

Storage device 216 may include a controller (not shown) and a computer readable medium 222 having instructions 224 capable of being executed by processor 202 to carry out functions of the throat microphone management application 150 and/or throat microphone application 175. In another implementation, some or all of the functions are carried out via hardware in lieu of a processor-based system. In one implementation, the controller included in storage device 216 is a web application browser, but in other implementations the controller may be a database system, a file system, an electronic mail system, a media manager, an image manager, or may include any other functions capable of accessing data items. Storage device 216 may also contain additional software and data (not shown), for implementing described features.

Output device 210 is configured to present information to the user. For example, output device 210 may be a display such as a liquid crystal display (LCD), a gas or plasma-based flat-panel display, or a traditional cathode-ray tube (CRT) display or other well-known type of display in the art of computer hardware. Accordingly, in some implementations output device 210 displays a user interface. In other implementations, output device 210 may be a speaker configured to output audible information to the user. In still other implementations, any combination of output devices may be represented by the output device 210.

Network interface 220 provides the computer system 200 with connectivity to the network 226 through any compatible communications protocol. Network interface 220 sends and/or receives data from the network 226 via a wireless or wired transceiver 214. Transceiver 214 may be a cellular frequency, radio frequency (RF), infrared (IR) or any of a number of known wireless or wired transmission systems capable of communicating with network 226 or other computer device having some or all of the features of computer system 200. Bus 208 may represent one or more busses, e.g., USB, PCI, ISA (Industry Standard Architecture), X-Bus, EISA (Extended Industry Standard Architecture), or any other appropriate bus and/or bridge (also called a bus controller). Network interface 220 as illustrated in FIG. 2 may be representative of a single network interface card configured to communicate with one or more different data sources.

Computer system 200 may be implemented using any suitable hardware and/or software, such as a personal computer or other electronic computing device. In addition, computer system 200 may also be a portable computer, laptop, tablet or notebook computer, PDA, pocket computer, appliance, telephone, server computer device, or mainframe computer.

Figure 3A:
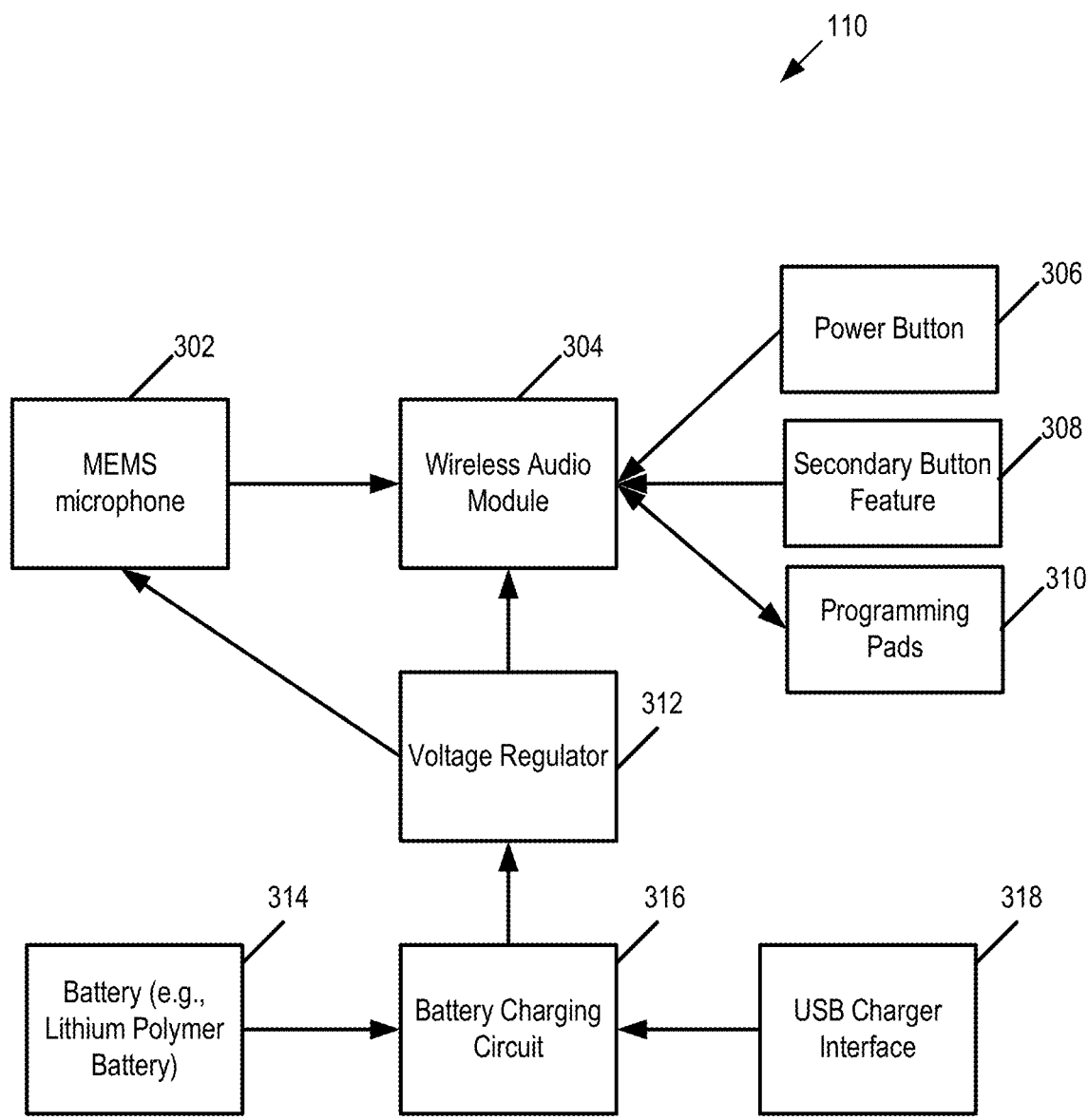
FIG. 3A is a first block diagram of the microphone unit.

FIG. 3A is a first block diagram of the microphone unit 110. Microphone unit includes MEMS microphone 302 (e.g., a MEMS digital microphone sensor configured to generate audio data), wireless audio module 304 (configured to communicate wirelessly with receiver unit 112), power button 306 (configured to turn the microphone unit 110 on and off), secondary button feature 308, programming pads 310, voltage regulator 312 (configured to regulate the voltage supplied by battery 314 to the desired voltage for the MEMS microphone 302 and wireless audio module 304), battery 314 (such as a Lithium Polymer battery), and battery charging circuit 316 (configured to receive charge via USB charger interface 318 in order to charge battery 314). Thus, the microphone unit 110 may include a microphone, such as MEMS microphone 302, which comprises a transducer to convert sound into an electrical signal. Alternatively, the USB charging circuit in microphone unit 110 may be replaced by an inductive charging receiver coil. Further, the receiver unit 112, discussed below with regard to element 506 to charge USB charging circuit, may be replaced by a charging coil.

The wireless audio module 304 may comprise a 2.4 GHz transceiver module (e.g., non-Bluetooth). In an alternative implementation, wireless audio module 304 may comprise Bluetooth communication in order to communicate directly with mobile electronic device 114, such as illustrated in FIG. 1D.

Figure 3B:
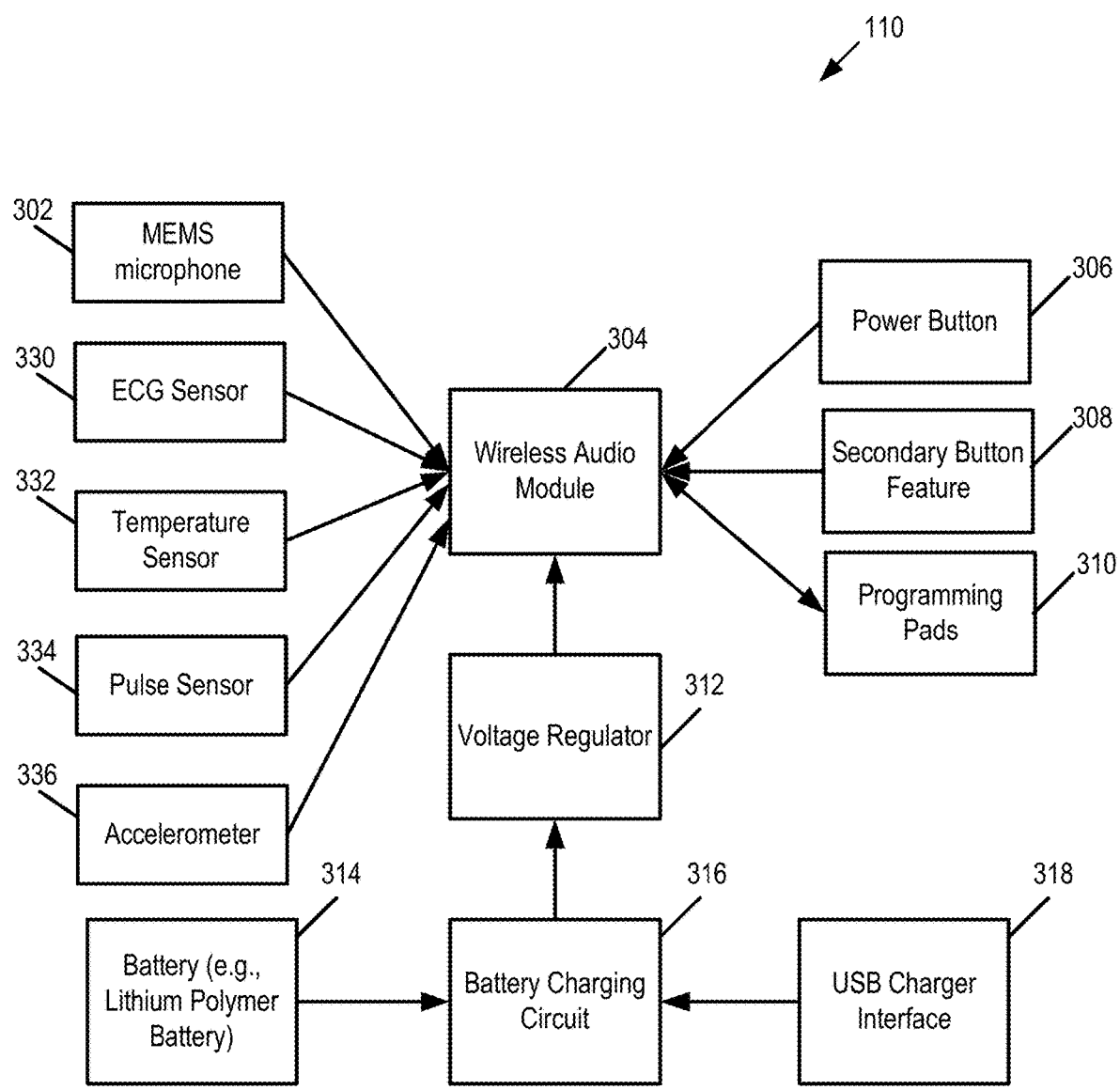
FIG. 3B is a second block diagram of the microphone unit with additional ECG, temperature, pulse and accelerometer sensors.

FIG. 3B is a second block diagram of the microphone unit with additional electrocardiography (ECG) 330, temperature 332, pulse 334, and accelerometer 336 sensors. Though not depicted, voltage regulator 312 may output the proper regulated voltage to each of MEMS microphone 302, temperature sensor 332, pulse sensor 334, and accelerometer 336. As discussed further below, one or more of the sensors depicted in FIG. 3B may be used in order to process the sound data, such as to voice unvoiced speech.

Thus, various sensors may be present in the microphone unit (such as microphone unit 110). For example, pulse sensor 334 may be resident in microphone unit 110. Pulse data, generated by pulse sensor 334, may be wirelessly transmitted to an external device, such as a heart monitor machine proximate to the patient (e.g., wirelessly transmit using Bluetooth) and/or such as to a back-end server for monitoring/archiving. In this way, because the microphone unit 110 is positioned on the throat and includes pulse sensor 334, an additional sensor to generate pulse data need not be used. Further, the data from the various sensors, including the voice stream and/or the pulse data, may be transmitted wirelessly to one or more electronic devices external to the microphone unit.

Similarly, the accelerometer data, such as generated by accelerometer 177, may be stored, such as locally in the microphone unit and/or in an external device (such as a back-end server). The stored accelerometer data may be analyzed in order to identify trends (e.g., increasing or decreasing tremors).

Figure 4:
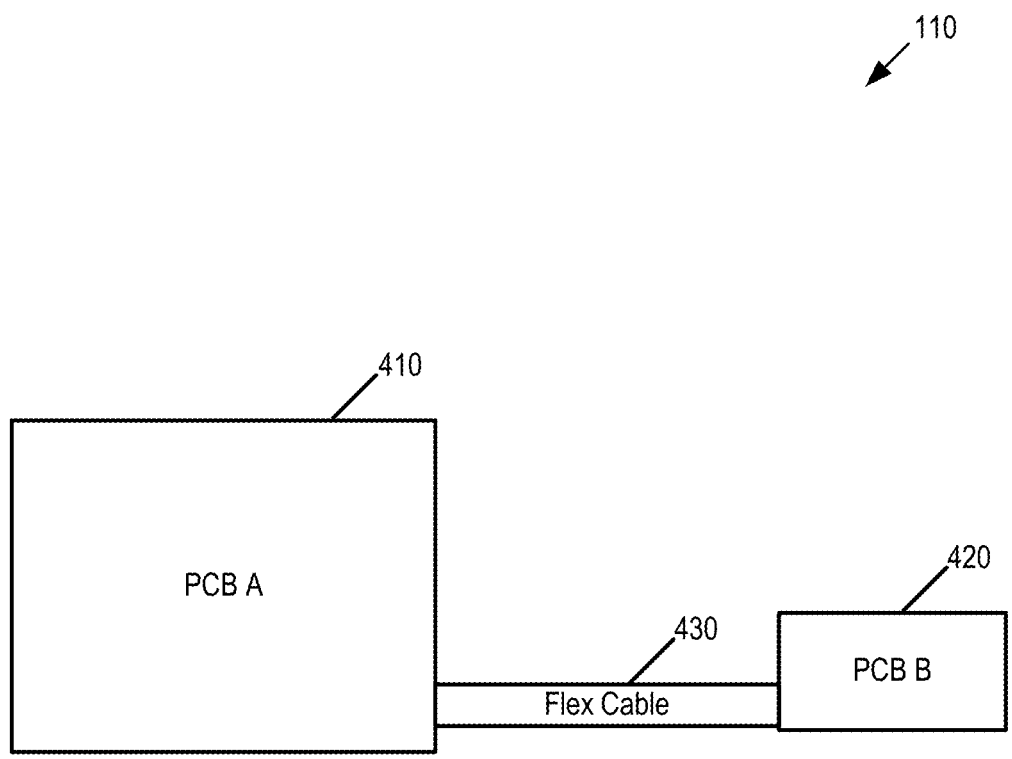
FIG. 4 is a third block diagram of the microphone unit illustrated as printed circuit boards electrically connected via a flex cable.

FIG. 4 is a second block diagram of the microphone unit 110. As illustrated, microphone unit 110 includes two printed circuit boards (PCBs), including PCB-A 410 and PCB-B 420. A flex cable 430 electrically connects PCB-A 410 and PCB-B 420. PCB-B 420 includes the MEMS microphone 302. PCB-A includes the remainder of the elements illustrated in FIG. 3A or in FIG. 3B. Microphone unit 110 may comprise two separate circuit boards connected via flex cable 430, which may be approximately 3 to 4 inches long in order for the microphone unit to bend around the neck of the wearer, such as illustrated in FIGS. 9A-D. Alternatively, microphone unit 110 may comprise a single circuit board.

Figure 5:
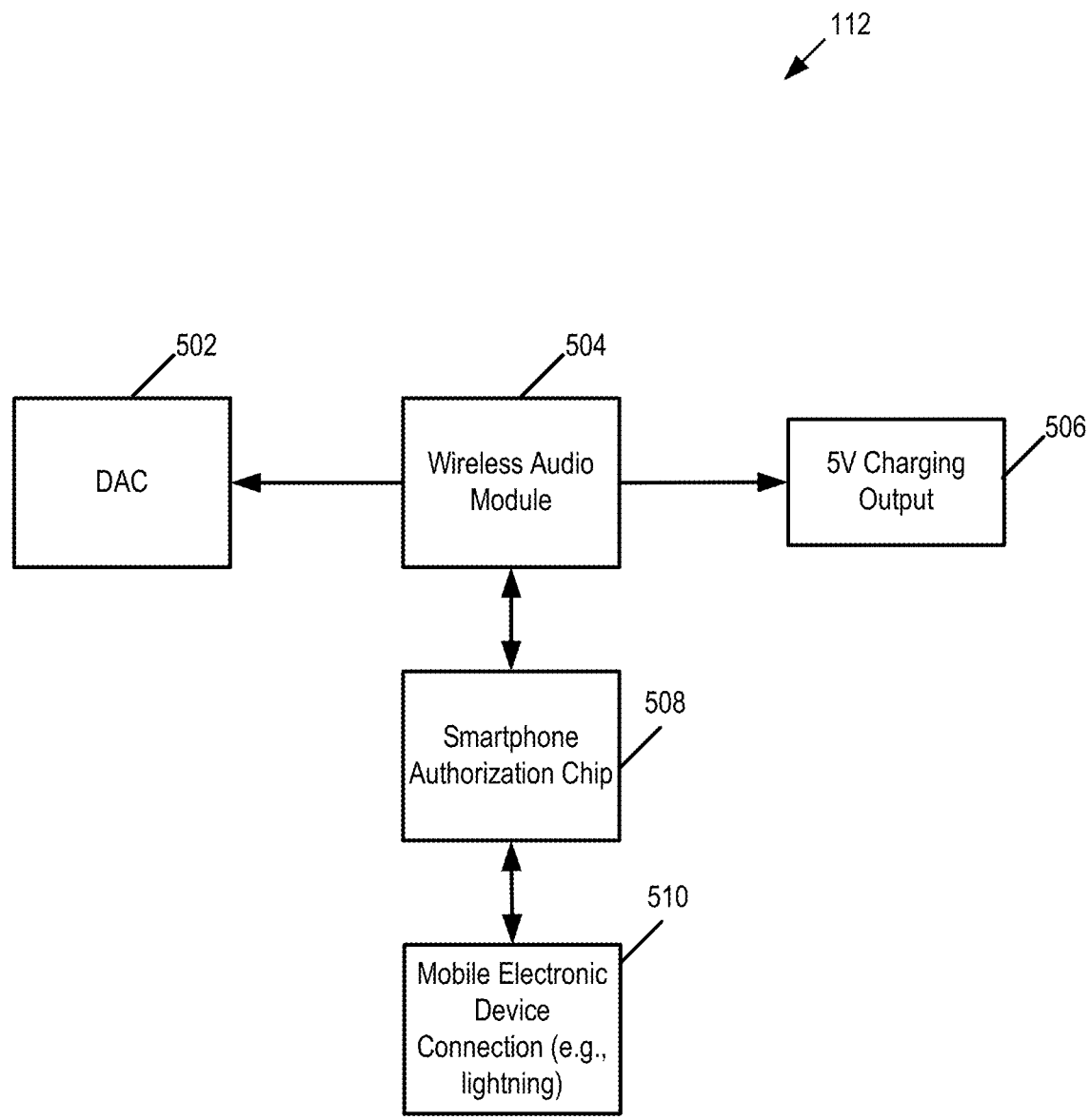
FIG. 5 is a block diagram of the receiver unit.

FIG. 5 is a block diagram of the receiver unit 112. Receiver unit 112 includes digital to analog converter 502 (configured to generate an analog audio signal for output on powered speaker 116), wireless audio module 504 (e.g., a 2.4 GHz transceiver module (non-Bluetooth)), charging output 506 (configured to charge microphone unit 110), smartphone authorization chip 508, and mobile electronic device connection 510 (such as a lighting connection), which may act as a smartphone interface. In this way, audio data, received by the receiver unit 112 from the microphone unit 110, may be streamed to the mobile electronic device 114. Further, the output of the DAC 502 may be connected to the powered speaker 116 in order to drive the powered speaker 116.

In one implementation, receiver unit 112 may comprise a single PCB comprising a 2.4 GHz transceiver module (which is non-Bluetooth), a smartphone (e.g., Apple iPhone) made for iPhone/iPod/iPad (MFi) circuit for lightning connection to iOS device, a DAC audio output to a speaker unit, and 5V output for charging of throat microphone.

As discussed above, microphone unit 110 may comprise a microphone (or other type of sound sensor) to generate sound data, and a transmitter to wirelessly transmit the sound data to an external electronic device. Further, the mobile electronic device 114 (such as a smartphone) may process the sound data in order to generate processed sound data (discussed in further detail below) for output. In one implementation, the microphone unit 110 may communicate indirectly with the mobile electronic device, such as via a receiver unit 112. For example, the mobile electronic device 114, such as the smartphone, includes a first wireless protocol (such as Bluetooth). Due to issues of latency with the first wireless protocol, the microphone unit communicates wirelessly with the receiver unit via a second protocol, with the smartphone being unable to communicate via the second protocol. Thus, in practice, the receiver unit 112, which is physically connected with the smartphone, acts as an intermediary, receiving the wireless transmission of the sound data in the second protocol from the microphone unit, and transmitting the sound data via a physical port to the smartphone for processing.

In one implementation, the receiver unit may act as a smartphone dock (such as a docking station), with the lightning connector being plugged into the smartphone. In this way, the smartphone may be physically connected with the docking station, with both remaining in fixed relation to one another. Alternatively, the receiver unit comprises a case into which the smartphone may be connected. In practice, the smartphone/receiver unit may be mobile as a smartphone typically is. In such an implementation, the smartphone/receiver unit may be placed inside a waterproof or water resistant enclosure. Thus, the smartphone/receiver unit may be protected in the event that the wearer accidentally spills water or food onto the smartphone/receiver unit.

When the receiver unit 112, via wireless audio module 504 resident in the receiver unit 112, receives the sound data, the receiver unit 112 transmits the sound data via a physical port (e.g., mobile electronic device connection 510). As discussed further below, the smartphone, executing an app, may then process the sound data, for output of the processed sound data to a speaker. In one implementation, the speaker may be connected to a device external to the smartphone (such as connected to the receiver unit). Alternatively, the speaker may be connected to or be in the smartphone. In either instance, the smartphone causes the processed sound data to be output via the speaker.

In one implementation, receiver unit 112 receives its power source from mobile electronic device 114 (e.g., via the lighting connector). Alternatively, receiver unit 112 may include its own power source.

Figure 6:
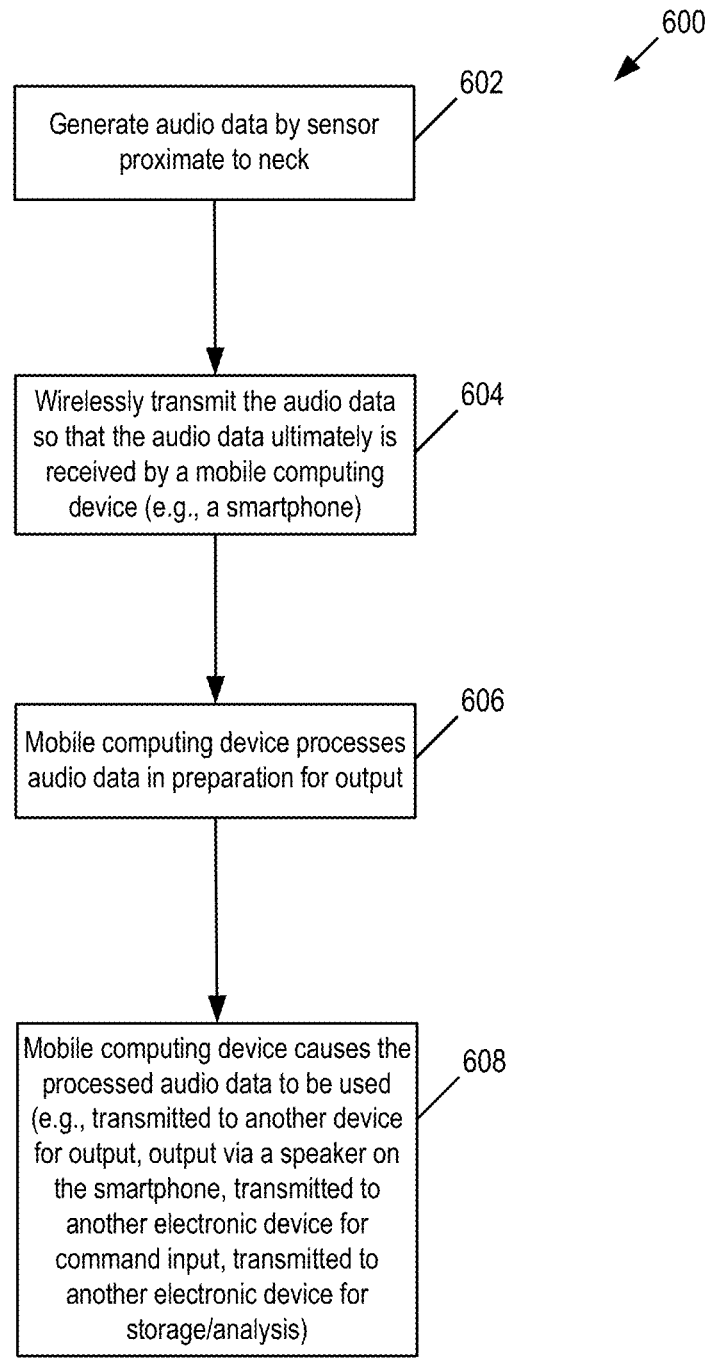
FIG. 6 is a first flow chart of audio data processing of the throat microphone system.

FIG. 6 is a first flow chart 600 of audio data processing of the throat microphone system. At 600, audio data is generated by a sensor proximate to the neck of the wearer. At 604, the audio data is wirelessly transmitted so that it is ultimately received by the mobile computing device. For example, the audio data may be transmitted via receiver unit, which in turn routes the audio data to the mobile computing device. Alternatively, the audio data may be transmitted from the microphone unit directly to the mobile computing device.

Figure 7:
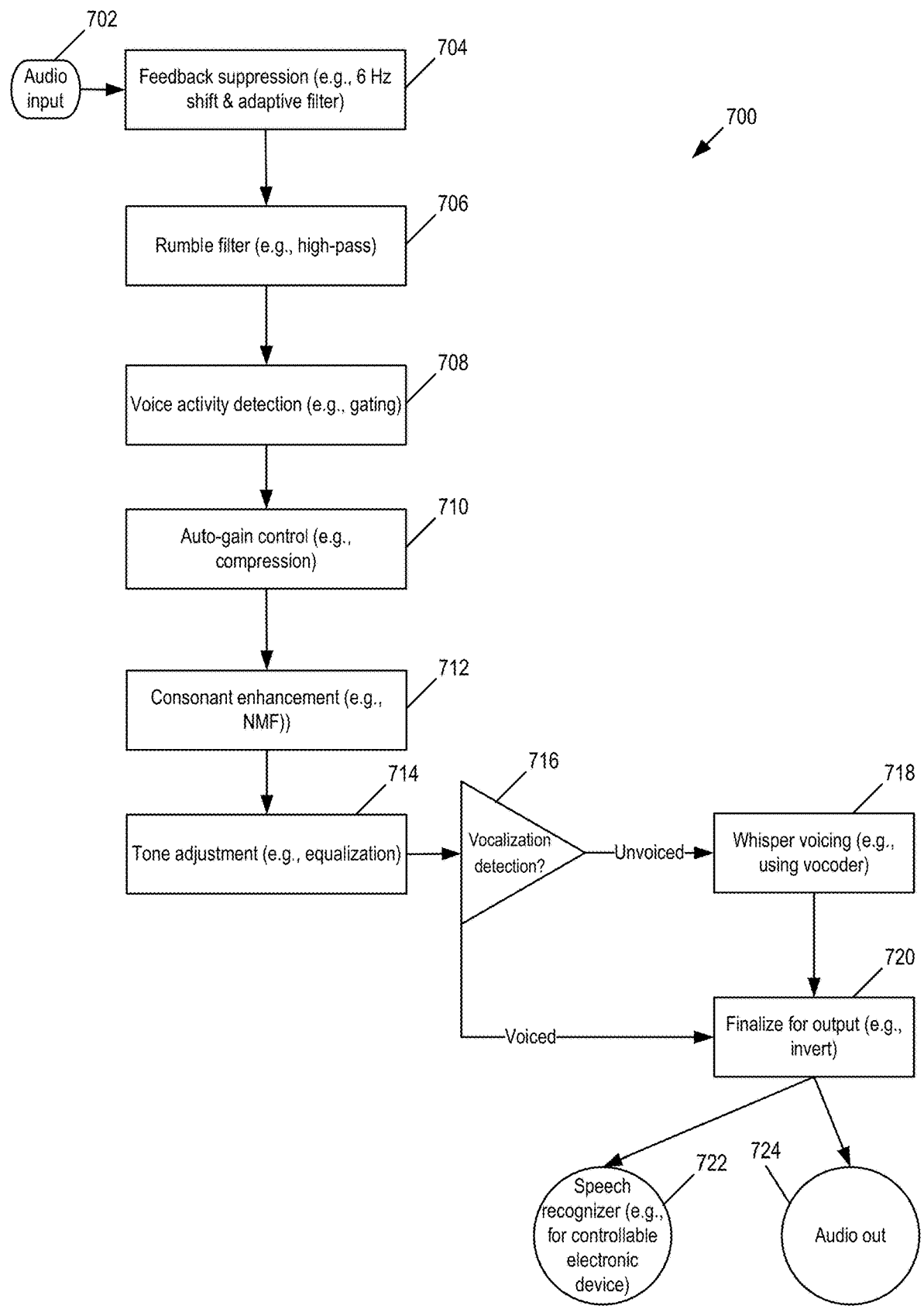
FIG. 7 is a second flow chart of audio data processing of the throat microphone system.

At 606, the mobile computing device processes the audio data in preparation for output, as discussed further in FIG. 7. At 608, the mobile computing device causes the processed audio data to be used in some form, such as transmitted to another device for output (e.g., output via powered speaker 116), output via a speaker on the smartphone, or transmitted to another electronic device (such as for command input or for storage and/or analysis by the another electronic device).

FIG. 7 is a second flow chart 700 of audio data processing of the throat microphone system. At 702, the audio data is input. At 704, the smartphone, such as an application ("app") executed on the smartphone, processes the audio input for feedback suppression. As one example, the app on the smartphone may perform a 6 Hz shift and an adaptive filter. Thus, in the instance where the speaker (such as powered speaker 116) is in the proximity of the microphone (such as the MEMS microphone), the feedback amongst the speaker and microphone may be reduced.

At 706, the app on the smartphone may use a rumble filter (e.g., a high-pass filter), thereby eliminating the noise resident in the lower end frequencies of the audio input, and thus potentially increasing the intelligibility of the audio input. As discussed above, one example parameter for the profile may include the cutoff frequency for the rumble filter.

At 708, voice activity detection is performed. In one implementation, voice activity detection may comprise gating in which it is determined that there is voice activity responsive to determining that the audio signal includes more than a threshold of voice activity (e.g., more than 5 dB within a certain frequency range) for at least a certain period of time. Thus, voice activity detection 708 may distinguish from voice present in the audio signal versus other sounds (such as a bump). Responsive to detecting voice activity in the audio input, gating may be used to turn on/off the audio input (with the audio input being effectively muted when gating turns off the audio input). Thus, in one implementation, the timing of the gating and/or the threshold of the gating may comprise parameters that may be assigned based on the assigned profile. In this way, the voice activity detection may detect whether there is a signal in the voice frequency range.

At 710, the auto-gain control is performed. For example, auto-gain control may be used to maintain the volume output at a consistent level. In one implementation, dynamic range compression may be used to compress the dynamic range (e.g., the volume may be kept within a predefined range, so that the high volumes (above the range) may be reduced and the low volumes (below the range) may be increased). Thus, in practice, responsive to the wearer becoming quieter, the auto-gain control may increase the volume output. Conversely, responsive to wearer becoming louder, the auto-gain control may decrease the volume output.

At 712, consonant enhancement is performed. For example, consonant enhancement may select certain consonants (e.g., sounds associated with "b" or "t") for emphasis using voice spectrum analysis and/or fast Fourier transforms. In this way, the intelligibility of the sound data may be increased. At 714, tone adjustment (such as equalization) is performed. For example, certain frequencies may be enhanced or reduced in order to shape the sound data.

At 716, it is determined whether to perform vocalization detection. As discussed above, depending on the parameters to configure the software in the smartphone, the vocalization detection may be always performed, never be performed, or be dynamically determined whether to perform. Thus, in one implementation, the vocalization detection 716 may be manifested as a software switch. For example, responsive to the wearer always (or consistently) whispering, vocalization detection 716 is always turned on. Conversely, responsive to the wearer consistently voicing his or her speech, vocalization detection 716 is always turned off (with 718 always being bypassed). Alternatively, the determination at 716 may be dynamic based on a real-time (or near real-time) analysis of the sound data of the wearer.

Dynamic determination of vocalization detection may examine one of several aspects in order to determine whether the wearer is vocalizing speech (e.g., whether the vocal chords are moving or not moving). Whispering is an example where vocalization is not occurring in that the vocal chords are not moving.

In one implementation, dynamic determination of vocalization detection comprises examining the power spectrum in order to determine whether the wearer is whispering. For example, the software may map out the speech in 2 dimensions and examine the voice spectrum (e.g., examine the strength in certain frequencies and/or certain key frequency ranges that are triggered when the sound is vocalized versus non-vocalized (e.g., a whisper)). In particular, whispering tends to have more power on the higher frequency ranges versus lower frequency ranges.

The analysis of the vocalization detection at 716 is different from the voice activity detection at 708 in their analysis as well as their effect on the logic flow. For example, vocalization detection at 716 comprises a voice spectrum analysis is configured to analyze for different things in order to switch on-off different things. In contrast, voice activity detection at 708 comprises gating to determine whether the audio signal includes more than a threshold of voice activity for at least a certain period of time. Further, vocalization detection at 716 determines whether to modify the voice signal at 718; if not, the processed voice signal is output. In contrast, voice activity detection at 708 determines whether to continue processing of the sound data responsive to determining that a voice signal is present is the sound data.

Responsive to determining at 716 to perform an analysis of the unvoiced sound (either based on a predetermined setting or based on a dynamic analysis), at 718, one or more aspects of the sound data are analyzed to determine whether unvoiced sound is present and if so, how to modify the audio data responsive to this determination (e.g., how to modify the audio data responsive to detecting whisper voicing). In one implementation, the analysis of the sound data to determine whether there is unvoiced speech may be based on one or more inputs, including any one, any combination, or all of: the sound data itself (e.g., the text of the speech generated by a speech recognizer; the speech power spectrum data; etc.); a current status of the wearer (e.g., the heart-rate of the speaker; the position of the speaker (e.g., lying down or sitting up); etc.

As one example, the software may identify text in the audio data (e.g., a transcription of the words). In particular, one implementation of the software comprises a machine learning engine, which may examine the audio data to identify one or more words in the sound data.

Responsive to identifying predetermined word(s) and/or a predetermined phrase (e.g., a set of words arranged in a predetermined order), the audio data may be modified. In particular, responsive to identifying that the text is indicative of a question, a vocoder (or other type of human voice synthesizer) may adjust the pitch of the carrier frequency (e.g., the sine wave) that is being vocoded. In particular, the vocoder may us a carrier sound (such as a sine wave of 1 KHz) and modulate the voice signal thereon. In order to reduce the tendency of vocoders to output robotic-like speech, the pitch of the carrier wave may be dynamically selected based on the content (e.g., the words) in the audio signal. Thus, in one implementation, the pitch of the sound data may be modified based on an analysis of the sound data (e.g., based on analysis of the words identified in the sound data).

For example, responsive to identifying that the voice data is indicative of a question (e.g., identifying "what" at the beginning of a phrase and/or identifying a set of words indicative of a question), the pitch for the carrier frequency may be increased when outputting the end of the phrase in order to provide an inflection indicative of a question. Thus, in certain languages and cultures, such as British or American English, the indication of a question comprises an increase in pitch at the end of the sentence. As discussed herein, the profile associated with the wearer may include an associated nationality. Thus, FIG. 7 illustrates one example of voicing of un-voiced speech using predictive inflection processing.

At 720, the signal is prepared for output. In one implementation, the signal may be inverted (e.g., flipped 180°) for feedback suppression. Alternatively, the signal may be transmitted for output without inversion.

At 722, the speech recognizer may provide a digital stream to an external electronic device (such as to an Amazon Alexa, etc.) and/or to the smartphone (such as to an app resident on the smartphone (e.g., "Hey Siri") or to the speaker on the smartphone). In this regard, the speech recognizer may perform customized wake-word detection in order to implement voice commands. For example, the speech recognizer may comprise an algorithm, such as a wake-word engine, that is constantly searching to identify a particular utterance which may last less than a second, in order to trigger the sending of a command to the external electronic device and/or to an app in the smartphone. The wake-word engine used by the speech recognizer may be tailored for this purpose in one or more respects including: (1) using input from those suffering from neurodegenerative diseases to train the wake-word engine; and/or (2) using input from a throat microphone system to train the wake-word engine. In this regard, the wake-word engine may be more adept to identify the wake-word(s) in the environment of its ultimate use. Thus, the speech recognizer may perform a separate function (e.g., wake work detection) for a different purpose (e.g., to command an external electronic device) than the function of identifying one or more words at 718 for the purpose of modifying the audio signal.

Responsive to identification of the wake word, the speech recognizer may perform one or more actions. For example, the speech recognizer may stream, via an application program interface (API), the remaining section of the audio signal (e.g., the audio signal without the "Alexa" utterance) as a digital stream to an external electronic device (such as to an Amazon Alexa). In this regard, a wearer may whisper or utter an Amazon Alexa command in order to transmit the command via the smartphone without requiring the wearer to shout directly to Alexa. As another example, the speech recognizer may stream the remaining section of the audio signal as a digital stream to a part of the smartphone (such as to the Siri application in the iPhone smartphone). As still another example, the speech recognizer may use the remaining section of the audio signal to control the app being executed on the smartphone to process the audio signal. In particular, the app performing the processing of the audio signal may be controlled via the utterance of a keyword (e.g., "Hey, Voco" (recognized by the app as a wake-word). Responsive to the speech recognizer recognizing the keyword, the speech recognizer may identify a command following the utterance of a keyword. The command may be directed to one or more aspects including: (1) configuration of the app (e.g., modification of one or more parameters that control processing of the app); and/or (2) handling of the processed audio signal (e.g., increasing the volume of the processed audio signal output in the instance where powered speaker 116 (e.g., "Hey, Voco—increase volume"); recording the processed audio signal (e.g., "Hey, Voco—start recording"; "Hey, Voco—stop recording"; "Hey, Voco—email recording")).

Any of blocks 704, 706, 708, 710, 712, 714, 716 illustrated in FIG. 7 may be activated or deactivated (e.g., bypassed) in software. For example, consonant enhancement at 712 may likewise be activated or deactivated based on the assigned profile. Further, fewer or greater processing steps than those depicted in FIG. 7 are contemplated. In addition, one, some or all of blocks 704, 706, 708, 710, 712, 714, 716 illustrated in FIG. 7 may be performed in receiver unit 112.

Figure 8A:
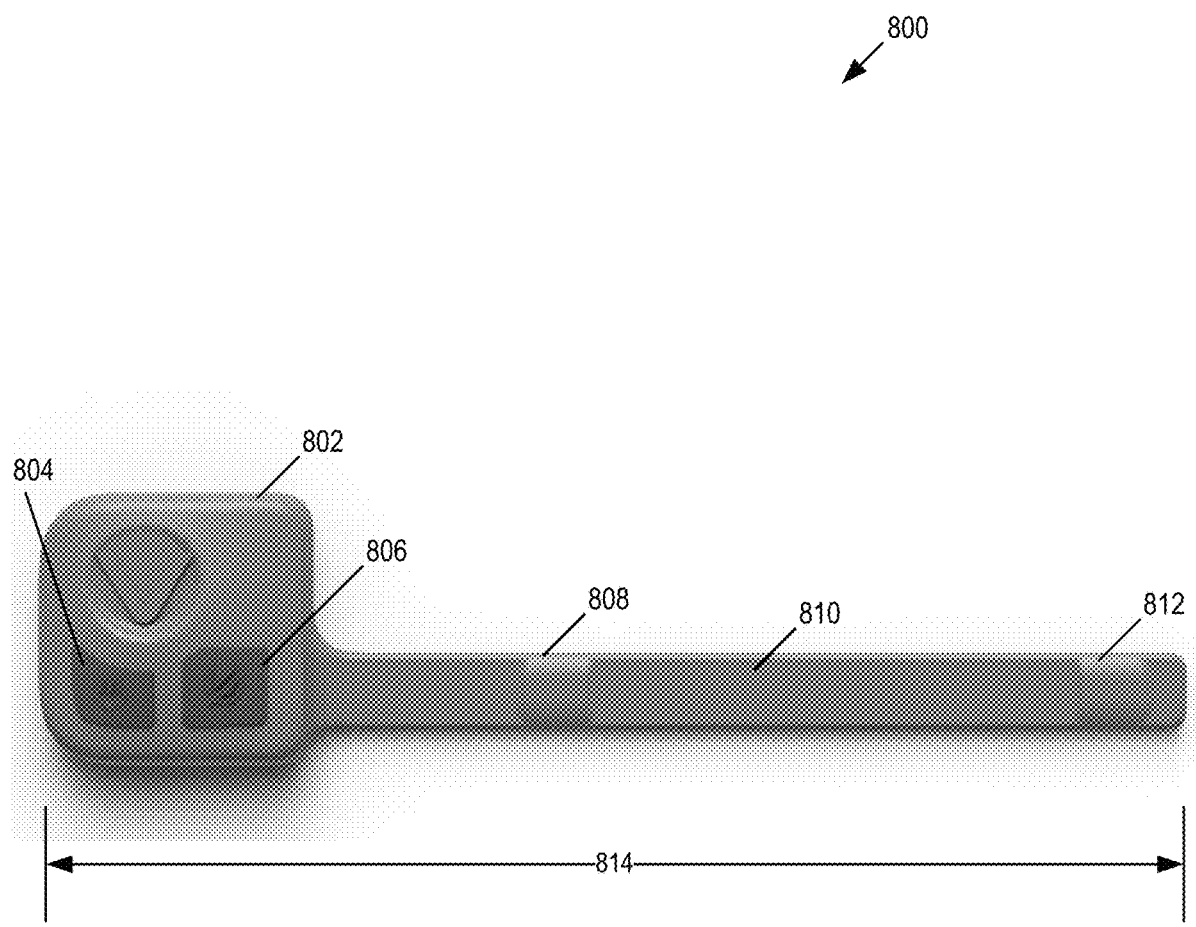
FIG. 8A is a front view of the microphone unit.
Figure 8B:
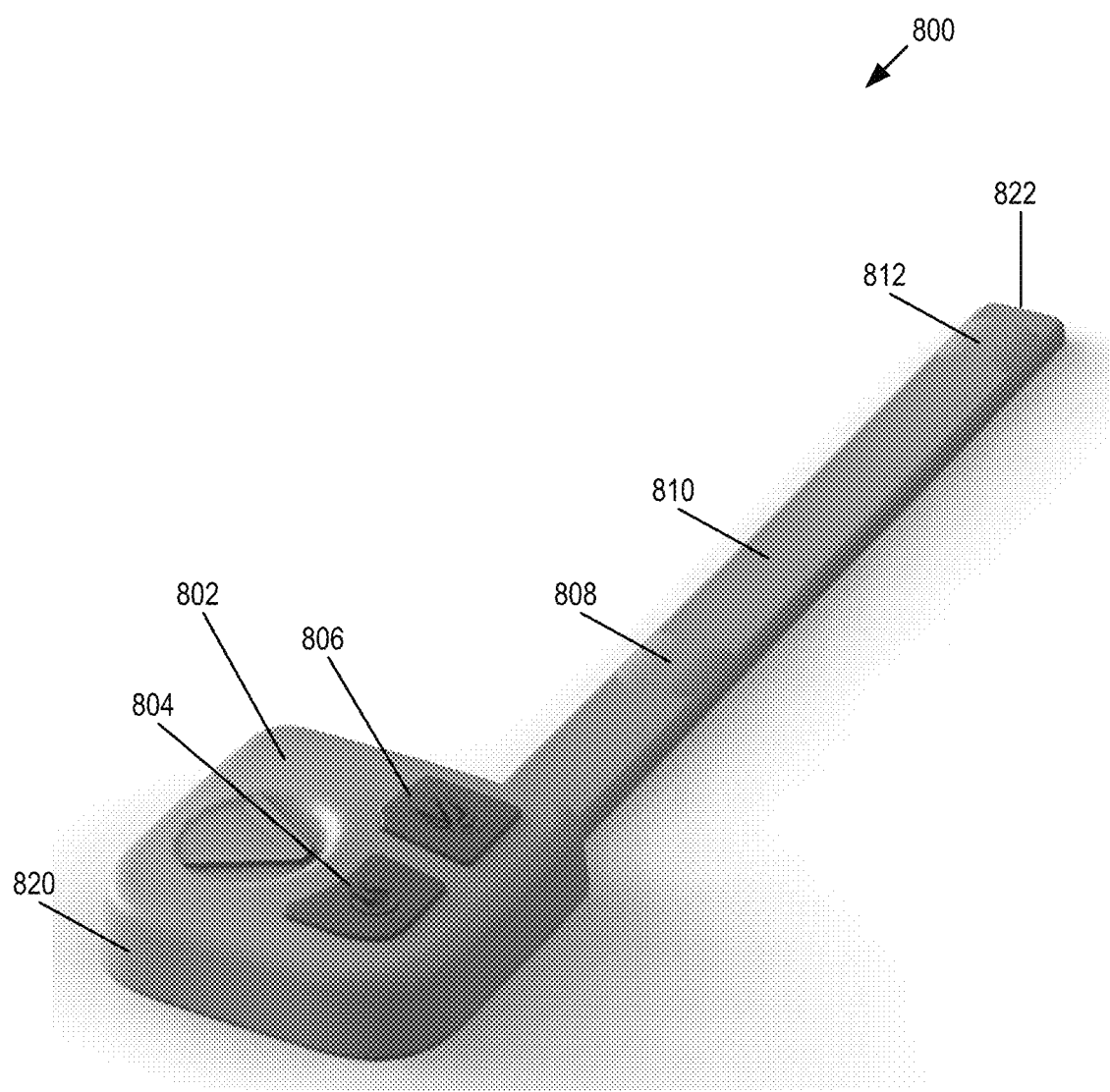
FIG. 8B is a front perspective view of the microphone unit.

FIG. 8A is a front view of the microphone unit 800. FIG. 8B is a front perspective view of the microphone unit 800. In one implementation, the microphone unit 800 has a total length of 814, and does not encircle the neck entirely. In this regard, in the event that the wearer is in distress, the microphone unit may be removed immediately with less effort. As shown in FIGS. 8A-B, main unit 802 may include PCB-A (such as illustrated in FIG. 4) and a battery, and may include buttons 804, 806 are resident on main unit 802. In one implementation, button 804 comprises an on/off button, and button 806 comprises a feature button, such as a mute button.

One, some, or all of microphone unit 800 may be encased in a rubber, such as silicone rubber. For example, in one implementation, each of the microphone unit (which may include one PCB), the flex ribbon cable, and the transmitter (which may include a second PCB and a battery) may be encased in an enclosure. Further, microphone unit 800 may include one microphone, two microphones, three microphones, etc. FIGS. 8A-B illustrate microphones 808, 812, each comprising a MEMS microphone element In this regard, the microphone unit 800 may include one or more microphones. In one implementation, the microphone unit includes a single microphone (e.g., a single MEMS microphone). The single microphone may generate a signal, such as a digital signal, representative of sensed sound proximate to or emanating from the throat.

In an alternate implementation, the microphone unit includes a plurality of microphones, such as two microphones, three microphones, or more. For example, in one implementation, the microphone unit includes a first microphone and a second microphone (e.g., a first MEMS microphone and a second MEMS microphone). The sensor data generated by the multiple microphones may be used for noise cancellation. As shown in FIGS. 8A-B, the second microphone may be positioned in a different part of the strip 810 of the microphone unit for noise cancellation purposes. In particular, processing, which may be performed at the mobile electronic device, may detect sound sensed at one microphone (e.g., one of the first microphone or the second microphone) that is not sensed by the other microphone (e.g., the other of the first microphone or the second microphone), and determine that sound detected at only one of the microphones (but not detected on both microphones) is considered noise. Conversely, processing may detect sound sensed at both microphones, and determine that sound at both of the microphones (e.g., is common to both microphones) is considered voice.

In a third implementation, the microphone unit may include a first microphone set (such as a single microphone, two microphones, etc.) and a second microphone set (such as a single microphone, two microphones, etc.). The first microphone set and the second microphone set differ in at least one aspect. One example differing aspect comprises the "pointing" direction of the microphones in the respective microphone set. In particular, the microphone(s) in the first microphone set may be positioned in the strip such that the microphone(s) are pointed inward (e.g., sensing sound perpendicular into the throat), whereas the microphone(s) in the second microphone set may be positioned in the strip such that the microphone(s) are pointed upward (e.g., positioned to point toward the mouth). Thus, the microphone(s) from the second microphone set may sense different sounds than the microphone(s) from the first microphone set, such as positioned to be able to better sense sounds emanating from the mouth of the wearer. In processing, the data from the different sets of microphones may be used to identify and capture articulation. In a specific implementation, two microphones may be used in the first microphone set for noise cancellation purposes and one or more microphones may be used in the second microphone set for articulation. Thus, in an implementation with multiple microphones, the multiple microphones may be positioned for a beamforming array in order to achieve spatial selectivity, thereby targeting the vocal chords.

Further, microphone unit 800 includes end 820 of main unit 802 and end 822 of strip 810. As shown, end 820 does not include clasp or connect to end 822. In this regard, end 820 and end 822 do not include any means for attachment, including no means for attaching end 820 to end 822 and vice-versa. In this way, the removal of the microphone unit 800 from the wearer is simplified.

Microphone unit 800 may be adhered to the body (such as adhered to the neck) in one of several ways. In one implementation, the microphone unit 800 may use an adhesive (such as die-cut double-sided adhesive) to adhere the microphone unit 800 to the neck of the wearer. For example, one, some or all of the main unit 802, the strip 810 and the microphone 808, 812 may be adhered to the wearer's neck via a die-cut double-sided adhesive strip. Alternatively, silicone (or other type of tacky material) may be used to contact the body (such as contact the neck). In still an alternative implementation, a base for use with the microphone unit may comprise on one side a pad of silicone used to adhere to the body and on the other side one or more magnets. The microphone unit may include opposite-poled magnets so that the microphone unit clicks onto the magnets on the base. In practice, the base may first be adhered to the neck of the user. Thereafter, the microphone unit may be snapped into the base.

Figure 9A:
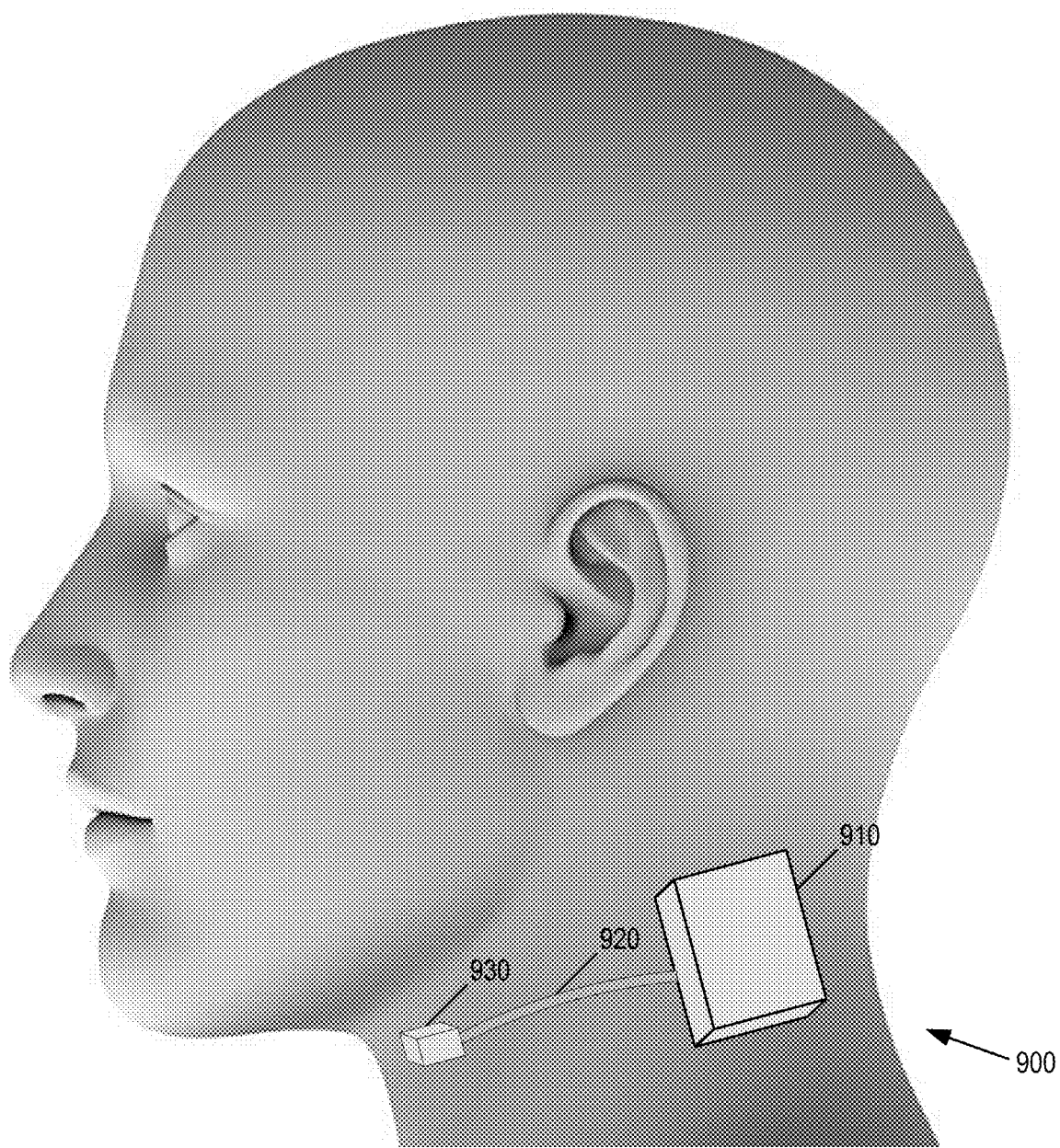
FIG. 9A is a side view of a human head model wearing the microphone unit.
Figure 9B:
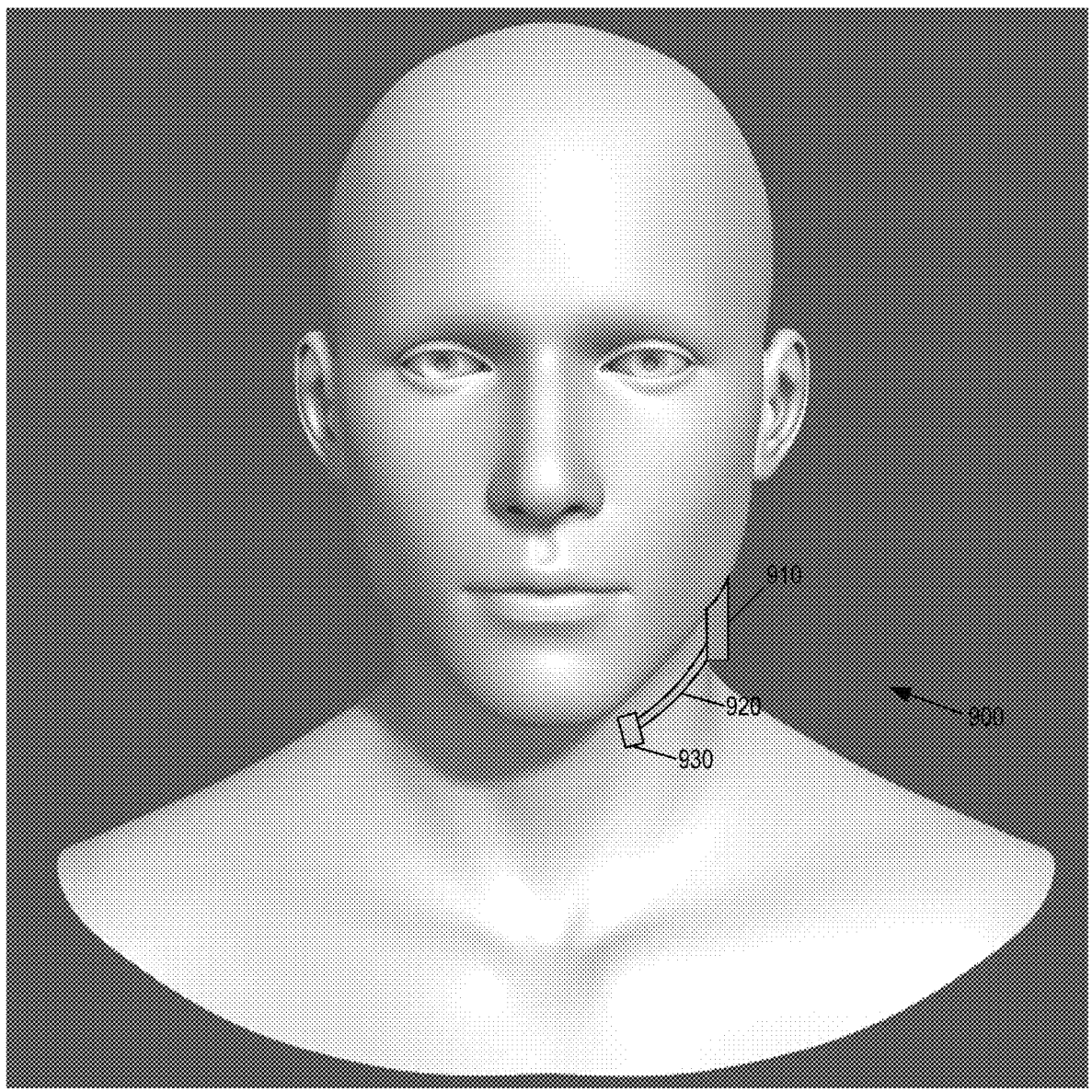
FIG. 9B is a front view of a human head model wearing the microphone unit.

FIG. 9A is a side view of a human head model wearing the microphone unit 900. FIG. 9B is a front view of a human head model wearing the microphone unit 900. As shown, microphone unit 900 includes main body 910, flexible conductive strip 920, and microphone 930.

Figure 9C:
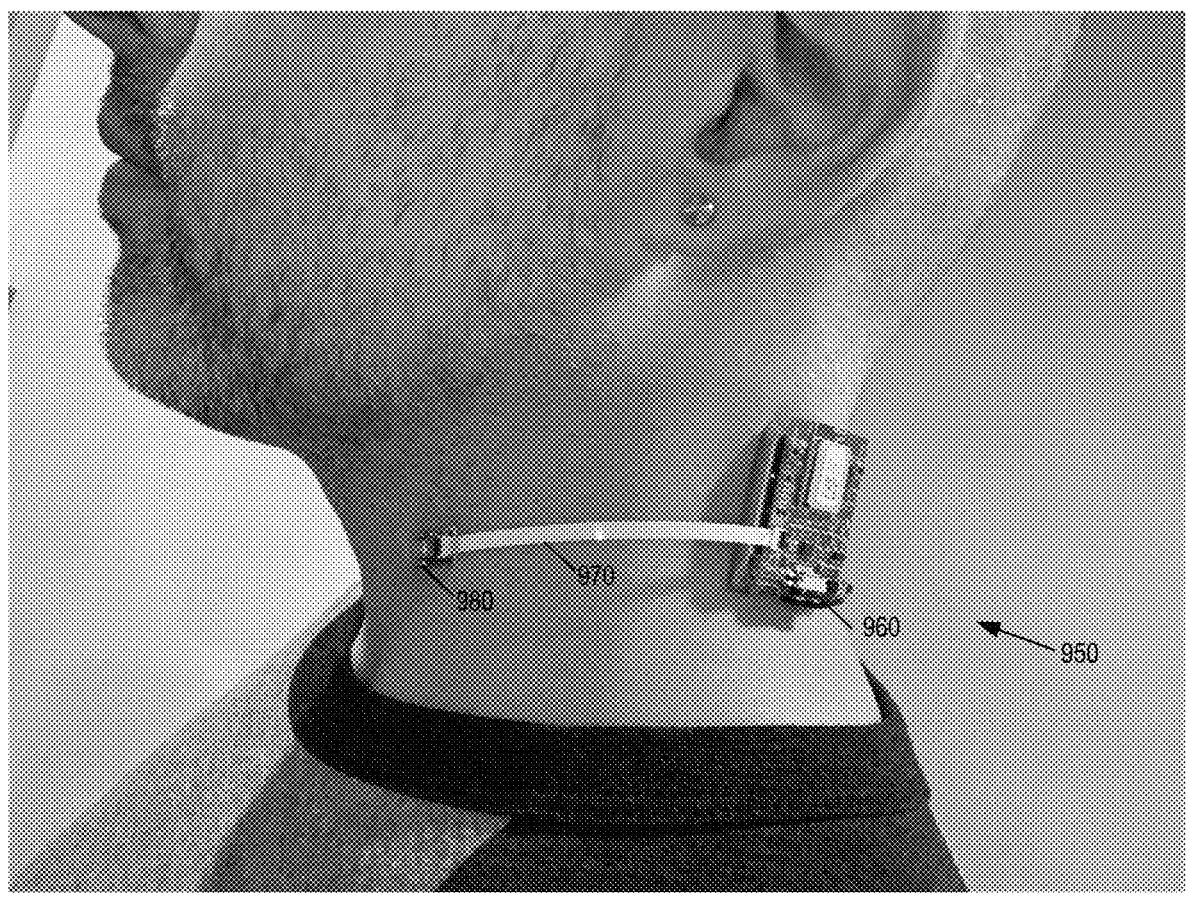
FIG. 9C is a side view of a human wearing the microphone unit.
Figure 9D:
FIG. 9D is a front view of a human wearing the microphone unit.

FIG. 9C is a side view of a human wearing the microphone unit 950. FIG. 9D is a front view of a human wearing the microphone unit 950. As shown, microphone unit 950 includes main body 960, flexible conductive strip 970, and microphone 980.

When the microphone unit 900, 950 is attached to the wearer, the portion of the microphone unit that houses that battery and transmitter is positioned below (such as approximately 3 inches below) the ear of the wearer, as shown in FIGS. 9A and 9C. Further, when the microphone unit 900, 950 is attached to the wearer, the microphone of the microphone unit may be positioned proximate to the larynx (including proximate to the vocal chords located directly behind the larynx). In males with a prominent Adam's apple, the microphone may be positioned to one side of the Adam's apple (such as the side of the Adam's apple closer to the main housing of the microphone unit). In females, with the external bump being much less visible and being hardly perceived on the upper edge of the thyroid cartilage, the microphone may be positioned in a similar manner to male wearers of the microphone unit 900, 950. Further, the position of the microphone 930, 980 is such that any feeding or ventilator tubes may be unobstructed.

In a first implementation, the microphone unit 900, 950 encircles less than 75% of the neck of the wearer. In a second implementation, the microphone unit 900, 950 encircles less than 50% of the neck of the wearer. In a third implementation, the microphone unit 900, 950 encircles less than 40% of the neck of the wearer. In a fourth implementation, the microphone unit 900, 950 encircles less than 30% of the neck of the wearer. In a fifth implementation, the microphone unit 900, 950 encircles less than 25% of the neck of the wearer. In a sixth implementation, the microphone unit 900, 950 encircles less than 20% of the neck of the wearer. In a seventh implementation, the microphone unit 900, 950 encircles less than 15% of the neck of the wearer. In an eighth implementation, the microphone unit 900, 950 encircles less than 10% of the neck of the wearer.

Figure 10A:
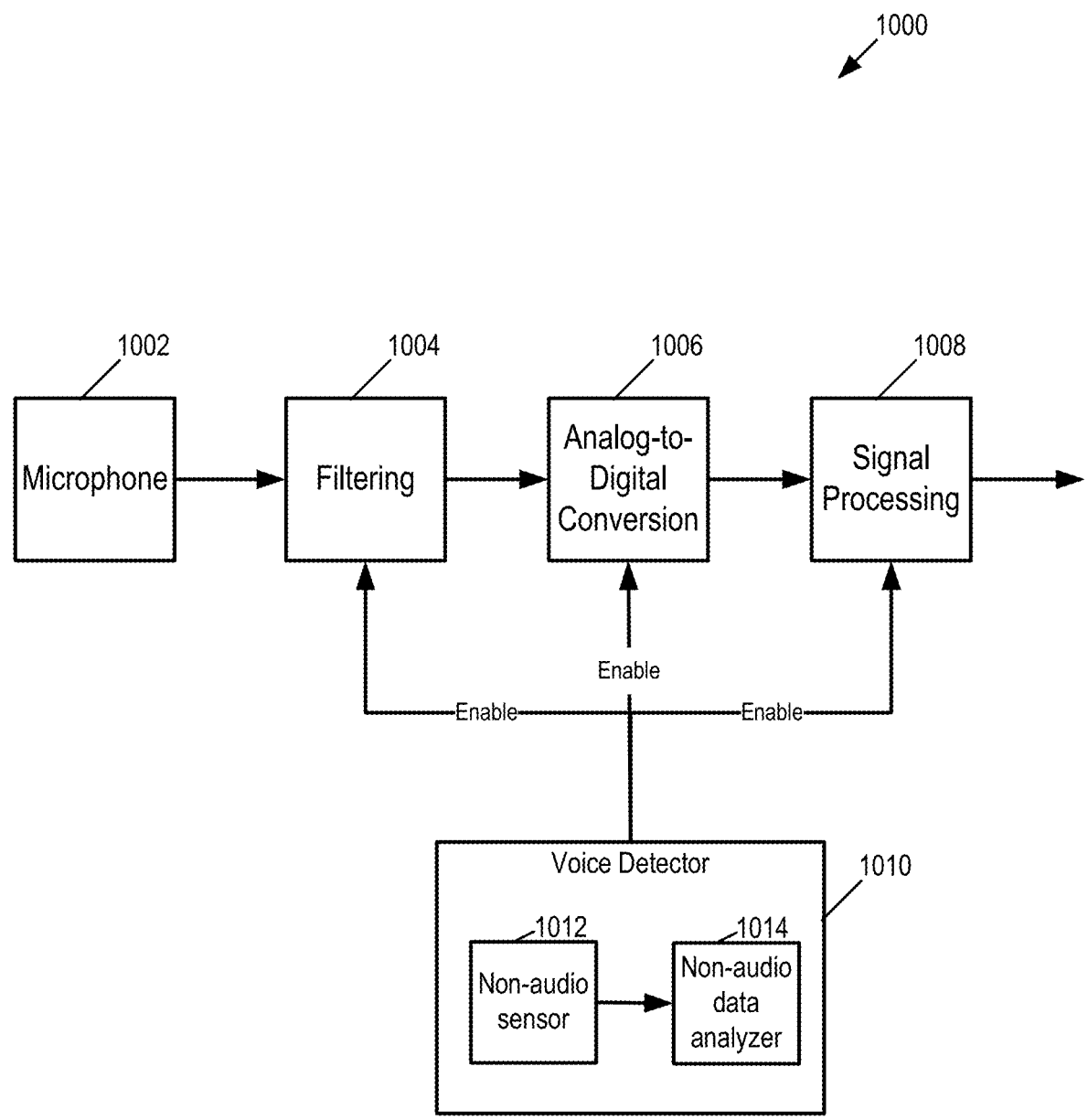
FIG. 10A is a first block diagram of a voice detector that uses non-audio data to detect whether voice is in data generated by a microphone.

FIG. 10A is a first block diagram 1000 of a voice detector 1010 that uses non-audio data to detect whether voice is in data generated by a microphone 1002. As shown, voice detector 1010 is configured to enable different parts of the circuit, such as filtering 1004 (configured to filter the audio signal generated by microphone 1002), analog-to-digital conversion (ADC) 1006, and signal processing 1008 (such as digital signal processing). Voice detector 1010 includes non-audio sensor 1012, which may comprise a vibration sensor or an electromyograph sensor, configured to generate sensed data, such as vibration data or an electromyogram. Non-audio data analyzer 1014 is configured to analyze the data in order to determine whether the data is indicative of the person speaking. If so, voice detector 1010 generates the enable signal to send to filtering 1004, ADC 1006, and signal processing 1008.

Figure 10B:
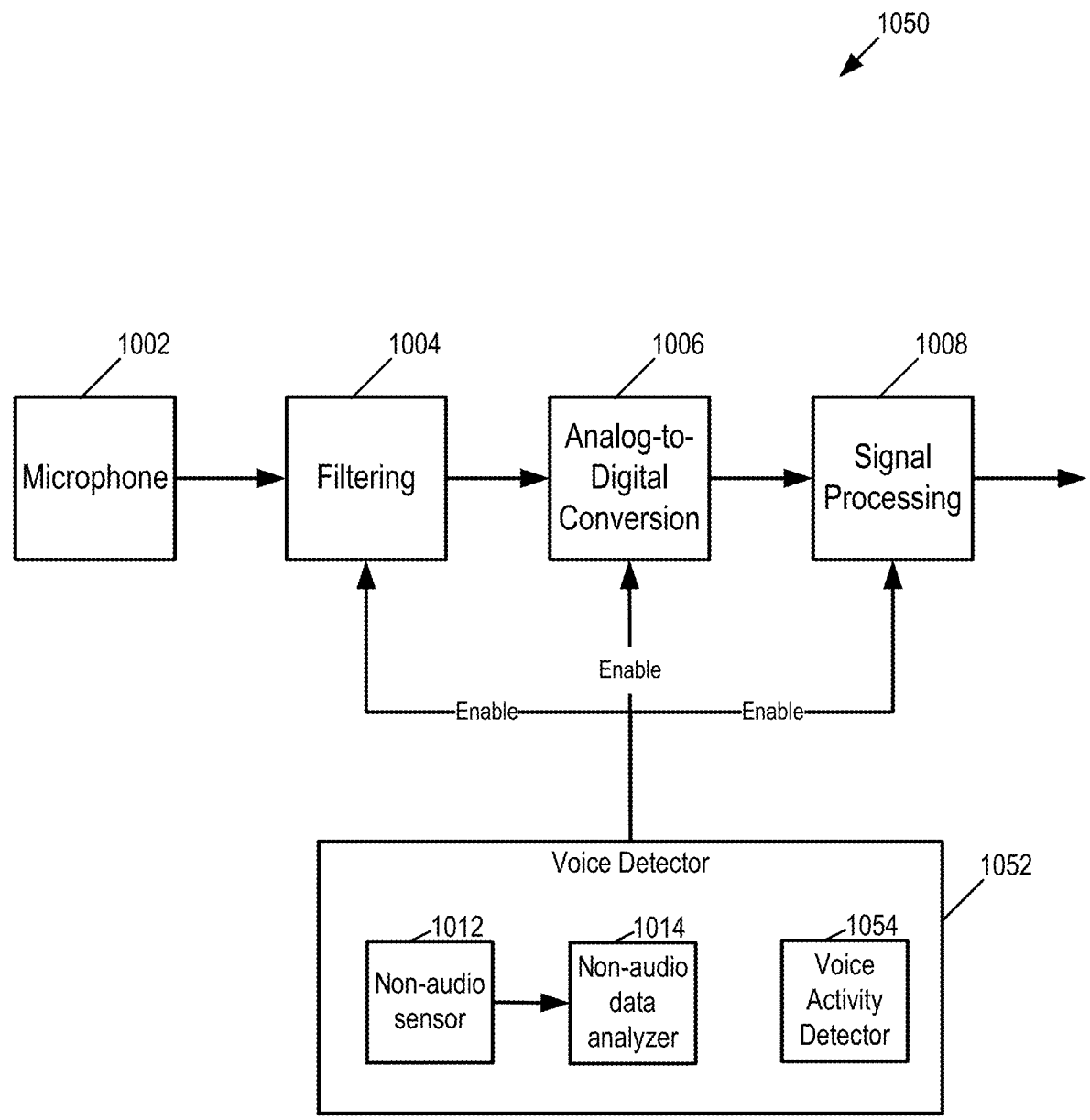
FIG. 10B is a second block diagram of a voice detector that uses non-audio data to detect whether voice is in data generated by a microphone.

FIG. 10B is a second block diagram 1050 of a voice detector 1052 that uses non-audio data to detect whether voice is in data generated by a microphone 1002. As shown, voice detector 1052 further includes voice activity detector (VAD) 1054.

VAD 1054 is configured to perform voice activity detection, also known as speech activity detection or speech detection. Voice activity detection is a technique used in speech processing in which the presence or absence of human speech is detected. VAD may comprise a vector or array signal, data, or information that in some manner represents the occurrence of speech in the digital or analog domain. As one example, an analog VAD 1054 may detect human speech by band-limiting the analog audio input signal from microphone 1002, compute signal energy within a given time window, and using the sequence of computed energy values, discriminate between ambient noise and human speech. One representation of VAD information is a one-bit digital signal sampled at the same rate as the corresponding acoustic signals, with a zero value representing that no speech has occurred during the corresponding time sample, and a unity value indicating that speech has occurred during the corresponding time sample. VAD may be applied in the digital domain or in the analog domain. Examples of voice activity detection are illustrated in US Patent Application Publication No. 2019/0198043 A1, US Patent Application Publication No. 2018/0315443 A1, US Patent Application Publication No. 2017/0092297 A1, U.S. Pat. No. 8,467,543, each of which are incorporated by reference herein in their entirety.

As discussed above, speech detection, such as by using non-audio data and/or VAD, may be used for several purposes, including for speech coding and speech recognition. Further, the speech detection may facilitate speech processing, and may also be used to deactivate some processes during non-speech section of an audio session (e.g., speech detection may avoid unnecessary coding/transmission of silence packets in Voice over Internet Protocol applications, saving on computation and on network bandwidth). Speech detection may further be used for noise reduction for digital hearing aid devices.

The present disclosure contemplates a computer-readable medium that includes instructions or receives and executes instructions responsive to a propagated signal, so that a device connected to a network can communicate voice, video, audio, images or any other data over the network. Further, the instructions can be transmitted or received over the network via a communication interface. The communication interface can be a part of the processor or can be a separate component. The communication interface can be created in software or can be a physical connection in hardware. The communication interface can be configured to connect with a network, external media, the display, or any other components in system, or combinations thereof. The connection with the network can be a physical connection, such as a wired Ethernet connection or can be established wirelessly as discussed below. In the case of a service provider server, the service provider server can communicate with users through the communication interface.

The computer-readable medium can be a single medium, or the computer-readable medium can be a single medium or multiple media, such as a centralized or distributed database, or associated caches and servers that store one or more sets of instructions. The term "computer-readable medium" can also include any medium that can be capable of storing, encoding or carrying a set of instructions for execution by a processor or that can cause a computer system to perform any one or more of the methods or operations disclosed herein.

The computer-readable medium can include a solid-state memory such as a memory card or other package that houses one or more non-volatile read-only memories. The computer-readable medium also can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an email or other self-contained information archive or set of archives can be considered a distribution medium that can be a tangible storage medium. The computer-readable medium is preferably a tangible storage medium. Accordingly, the disclosure can be considered to include any one or more of a computer-readable medium or a distribution medium and other equivalents and successor media, in which data or instructions can be stored.

Alternatively, or in addition, dedicated hardware implementations, such as application specific integrated circuits, programmable logic arrays and other hardware devices, can be constructed to implement one or more of the methods described herein. Applications that can include the apparatus and systems of various embodiments can broadly include a variety of electronic and computer systems. One or more embodiments described herein can implement functions using two or more specific interconnected hardware modules or devices with related control and data signals that can be communicated between and through the modules, or as portions of an application-specific integrated circuit. Accordingly, the present system can encompass software, firmware, and hardware implementations.

The methods described herein may be implemented by software programs executable by a computer system. Further, implementations may include distributed processing, component/object distributed processing, and parallel processing. Alternatively, or in addition, virtual computer system processing may be constructed to implement one or more of the methods or functionality as described herein.

Although components and functions are described that may be implemented in particular embodiments with reference to particular standards and protocols, the components and functions are not limited to such standards and protocols. For example, standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

The following example embodiments of the invention are also disclosed:

Embodiment 1

A throat microphone system comprising:
a microphone unit configured to attach to a throat of a person, the microphone unit comprising a microphone configured to generate sound data and wireless communication functionality configured to transmit the sound data wirelessly; and
at least one electronic device configured to:
receive the wirelessly transmitted sound data;
process the sound data by modifying the sound data in an audio range in order to generate processed sound data; and
cause output or transmission of at least a part of the processed sound data.

Embodiment 2

The throat microphone system of embodiment 1:
wherein the at least one electronic device comprises a smartphone with communication functionality, the communication functionality configured to communicate with an external electronic device; and
wherein the smartphone is configured to cause the output or transmission of at least a part of the processed sound data by transmitting, using the communication functionality, the at least a part of the processed sound data to the external electronic device.

Embodiment 3

The throat microphone system of any of embodiments 1 or 2,
wherein the communication functionality comprises Internet communication functionality;
wherein the external electronic device comprises a server; and wherein the smartphone is configured to transmit the processed sound data to the server for at least one of storage or analysis.

Embodiment 4

The throat microphone system of any of embodiments 1-3,
- wherein the at least one electronic device comprises a receiver unit configured to communicate with the microphone unit in a particular near-field communication protocol and a smartphone;
- wherein the receiver unit is in wired connection with the smartphone;
- wherein the smartphone consists of communication functionality that does not include the particular near-field communication protocol; and
- wherein the smartphone is configured to cause the output or transmission of at least a part of the processed sound data by causing the at least a part of the processed sound data to be output via a speaker.

Embodiment 5

The throat microphone system of any of embodiments 1-4,
- further comprising the speaker, the speaker being driven by the receiver unit; and
- wherein the smartphone is configured to cause the at least a part of the processed sound data to be output via the speaker by transmitting the at least a part of the processed sound data to the receiver unit in order for the receiver unit to drive the speaker with the at least a part of the processed sound data.

Embodiment 6

The throat microphone system of any of embodiments 1-5,
- wherein the at least one electronic device is configured to process the sound data by:
- analyzing the sound data in order to detect an indication of a command word; and
- responsive to detecting the indication of the command word, cause a command in the sound data to be implemented.

Embodiment 7

The throat microphone system of any of embodiments 1-6,
- wherein the indication of a command word comprises a wake word for an external device; and
- wherein the at least one electronic device is configured to, responsive to identifying the wake word, cause the command in the sound data to be implemented by transmitting at least a part of the sound data to the external device in order for the external device to implement the command.

Embodiment 8

The throat microphone system of any of embodiments 1-7,
- wherein the at least one electronic device is configured to process the sound data using one or more parameters;
- wherein the indication of a command word comprises a wake word for the at least one electronic device; and
- wherein the at least one electronic device is configured to, responsive to identifying the wake word, cause the command in the sound data to be implemented by modifying the one or more parameters or by recording the sound data based on the command.

Embodiment 9

The throat microphone system of any of embodiments 1-8,
- wherein the at least one electronic device comprises a smartphone with a memory, the memory configured to store a plurality of profiles, each of the plurality of profiles correlated to one or both of an aspect relating to a wearer of the microphone unit or environment in which the throat microphone system is used, each of the plurality of profiles including one or more parameters selected based on the aspect relating to the wearer or the environment in which the throat microphone system is used;
- wherein the smartphone is further configured to select a particular profile, from the plurality of profiles; and
- wherein the smartphone is configured to process the sound data using the one or more parameters in the selected particular profile.

Embodiment 10

The throat microphone system of any of embodiments 1-9,
- wherein the at least one electronic device comprises a smartphone; and
- wherein the smartphone is configured to process the sound data by performing: high-pass filtering; voice activity detection; auto-gain control; and tone adjustment.

Embodiment 11

The throat microphone system of any of embodiments 1-10,
- wherein the smartphone is further configured to process the sound data by modifying the sound data based on unvoiced speech detected in the sound data.

Embodiment 12

A throat microphone processing system comprising:
- an interface configured to receive sound data from a throat microphone; and
- a processor configured to:
  - analyze at least one aspect of non-vocalized speech in the sound data;
  - responsive to analyzing the at least one aspect of the non-vocalized speech in the sound data, modify the sound data in order to vocalize the non-vocalized speech; and
  - causing the modified sound data to be output on a speaker in order to vocalize the non-vocalized speech.

Embodiment 13

The throat microphone system of embodiment 12:
wherein the processor is further configured to determine whether to perform the analysis of the at least one aspect of the non-vocalized speech in the sound data; and
wherein the processor is configured to analyze the at least one aspect of the non-vocalized speech in the sound data responsive to determining to perform the analysis.

Embodiment 14

The throat microphone system of any of embodiments 12 or 13,
wherein the processor is configured to analyze the at least one aspect of non-vocalized speech in the sound data by:
generating text from the sound data; and
analyzing the text to determine whether there is non-vocalized speech in the sound data.

Embodiment 15

The throat microphone system of any of embodiments 12-14,
wherein the processor is configured to analyze the at least one aspect of non-vocalized speech in the sound data by:
analyzing speech power spectrum data of the sound data.

Embodiment 16

The throat microphone system of any of embodiments 12-15,
wherein the processor is configured to determine whether there is non-vocalized speech in the sound data by:
analyzing the at least one aspect of non-vocalized speech in the sound data; and
analyzing data from at least one non-microphone sensor.

Embodiment 17

The throat microphone system of any of embodiments 12-16,
wherein the processor is configured to analyze the data from at least one non-microphone sensor by analyzing data indicative of a heart-rate of a person generating the sound data.

Embodiment 18

The throat microphone system of any of embodiments 12-17,
wherein the processor is configured to modify the sound data in order to vocalize the non-vocalized speech by modifying pitch of a carrier signal, the carrier signal used to output the sound data.

Embodiment 19

A throat microphone processing system comprising:
an interface configured to receive sound data from a throat microphone and receive non-sound data regarding a wearer of the throat microphone; and
a processor configured to:
analyze at least one aspect of non-vocalized speech in the sound data;
analyze at least one aspect of the non-sound data;
responsive to analyzing the at least one aspect of the non-vocalized speech in the sound data and to analyzing the at least one aspect of the non-sound data, modify the sound data in order to vocalize the non-vocalized speech; and
causing the modified sound data to be output on a speaker in order to vocalize the non-vocalized speech.

Embodiment 20

The throat microphone processing system of embodiment 19,
wherein the non-sound data comprises data indicative of a heart-rate of a person generating the sound data.

Embodiment 21

A throat microphone unit comprising:
a housing comprising an adhesive and configured for contact with a throat of a wearer such that the throat microphone unit when attached via the adhesive to a neck of the wearer does not encircle a perimeter of the neck of the wearer;
at least one microphone in the housing, the microphone configured to generate sound data emanating from the throat of the wearer of the throat microphone unit; and
a wireless transceiver in the housing and in electrical communication with the at least one microphone.

Embodiment 22

The throat microphone unit of embodiment 21,
wherein the housing is configured to encircle less than half of the perimeter of the neck of the wearer.

Embodiment 23

The throat microphone unit of embodiment 21,
wherein the housing is configured to encircle less than one-quarter of the perimeter of the neck of the wearer.

Embodiment 24

The throat microphone unit of any of embodiments 21-23,
wherein the wireless transceiver and the at least one microphone are in electrical communication via at least one wire;
wherein the at least one wire comprises a flexible cable electrically connecting the microphone to the wireless transceiver; and
wherein the housing includes a main unit configured to house the wireless transceiver, a strip configured to house the flexible cable, and a sensor unit configured to house the microphone.

Embodiment 25

The throat microphone unit of any of embodiments 21-24,
wherein the throat microphone unit includes a first MEMS microphone configured to generate first sound data and a second MEMS microphone configured to generate second sound data; and wherein the wireless transceiver is configured to transmit the first sound data and the second sound data in order for an external electronic device to perform noise cancellation by analyzing the first sound data and the second sound data.

Embodiment 26

The throat microphone unit of any of embodiments 21-25, wherein the throat microphone unit includes a third microphone;
wherein the first MEMS microphone and the second MEMS microphone are positioned in the housing such that, when the throat microphone unit is worn, the first MEMS microphone and the second MEMS microphone point inward to a neck of the wearer; and
wherein the third microphone is positioned in the housing such that, when the throat microphone unit is worn, the third microphone and points upward to a mouth of the wearer.

Embodiment 27

A microphone unit comprising:
a microphone configured for attachment on or proximate a person and configured to generate audio data;
a sensor configured for contact on at least a part of a throat of a person and configured to generate sensor data indicative of movement associated with speech generated by the person; and
at least one processor in communication with microphone and the sensor, the at least one processor configured to:
analyze the sensor data in order to determine whether the sensor data is indicative that the person is generating the speech; and
responsive to determining that the sensor data is indicative that the person is generating the speech, process the audio data.

Embodiment 28

The microphone unit of embodiment 27,
wherein the sensor comprises a sensor configured to sense vibrations associated with the at least a part of the throat of the person.

Embodiment 29

The microphone unit of any of embodiments 27 or 28,
wherein the sensor comprises an electromyography sensor configured to generate data indicative of movement of at least one muscle in the throat of the person.

Embodiment 30

The microphone unit of any of embodiments 27-29,
wherein the at least one processor is configured to analyze the sensor data in order to determine whether the sensor data is indicative that the person is generating the speech by:
determining whether an amplitude associated with the sensor data is greater than or equal to a threshold; and
responsive to determining that the amplitude associated with the sensor data is greater than or equal to the threshold, determining that the sensor data is indicative that the person is generating the speech.

Embodiment 31

The microphone unit of any of embodiments 27-30,
wherein the at least one processor is configured to process the audio data by causing an output, based on the audio data, to be generated on at least one speaker.

Embodiment 32

The microphone unit of any of embodiments 27-31,
wherein the at least one processor is configured to process the audio data by causing an electronic transmission, based on the audio data, to an electronic device external to the microphone unit.

Embodiment 33

The microphone unit of any of embodiments 27-32,
wherein the microphone configured for attachment on the throat of the person.

Embodiment 34

The microphone unit of any of embodiments 27-33,
further comprising a housing configured for attachment to the throat of the person; and
wherein the microphone and the sensor are at least partly within the housing.

Embodiment 35

The microphone unit of any of embodiments 27-34,
wherein the at least one processor is further configured to perform voice activity detection in order to detect voice in the audio data; and
wherein the at least one processor is configured to determine whether the sensor data is indicative that the person is generating the speech based on both the analysis of the sensor data and based on the voice activity detection.

Embodiment 36

A microphone unit comprising:
a microphone configured for attachment on or proximate a person and configured to generate audio data;
a sensor configured for positioning at least partly inside the person and configured to generate sensor data; and
at least one processor in communication with microphone and the sensor, the at least one processor configured to:
analyze the sensor data in order to determine whether the sensor data is indicative that the person is generating the speech; and
responsive to determining that the sensor data is indicative that the person is generating the speech, process the audio data.

Embodiment 37

The microphone unit of embodiment 36,
wherein the sensor comprises a vibration sensor configured to generate vibration sensor data; and wherein the at least one processor is configured to analyze the sensor data by analyzing whether the vibration sensor data is indicative of the person generating the speech.

Embodiment 38

The microphone unit of any of embodiments 36 or 37, wherein the sensor is configured for positioning at least partly in an ear canal of the person.

Embodiment 39

The microphone unit of any of embodiments 36-38, further comprising an earpiece including a speaker;
wherein the sensor is housed at least partly in the earpiece; and
wherein the processor is configured to process the audio data by:
responsive to determining that the vibration sensor data is indicative of the person generating the speech, ceasing output of the audio data via the speaker in the earpiece.

Embodiment 40

The microphone unit of any of embodiments 36-39, wherein the at least one processor is further configured to perform voice activity detection in order to detect voice in the audio data; and
wherein the at least one processor is configured to determine whether the sensor data is indicative that the person is generating the speech based on both the analysis of the sensor data and based on the voice activity detection.

The illustrations described herein are intended to provide a general understanding of the structure of various embodiments. The illustrations are not intended to serve as a complete description of all of the elements and features of apparatus, processors, and systems that utilize the structures or methods described herein. Many other embodiments can be apparent to those of skill in the art upon reviewing the disclosure. Other embodiments can be utilized and derived from the disclosure, such that structural and logical substitutions and changes can be made without departing from the scope of the disclosure. Additionally, the illustrations are merely representational and cannot be drawn to scale. Certain proportions within the illustrations may be exaggerated, while other proportions may be minimized. Accordingly, the disclosure and the figures are to be regarded as illustrative rather than restrictive.

The above disclosed subject matter is to be considered illustrative, and not restrictive, and the appended claims are intended to cover all such modifications, enhancements, and other embodiments, which fall within the true spirit and scope of the description. Thus, to the maximum extent allowed by law, the scope is to be determined by the broadest permissible interpretation of the following claims and their equivalents, and shall not be restricted or limited by the foregoing detailed description.

The invention claimed is:

1. A throat microphone unit comprising:
a housing configured for contact with a throat of a wearer such that the throat microphone unit when attached to a neck of the wearer does not encircle a perimeter of the neck of the wearer;
at least one microphone in the housing, the microphone configured to generate sound data emanating from the throat of the wearer of the throat microphone unit, wherein the at least one microphone comprises a first microphone configured to generate first sound data and a second microphone configured to generate second sound data; and
a wireless transceiver in the housing and in electrical communication with the at least one microphone in order to transmit the first sound data and the second sound data in order for an external electronic device to perform noise cancellation by analyzing the first sound data and the second sound data.

2. The throat microphone unit of claim 1, wherein the housing is configured to encircle less than one-quarter of the perimeter of the neck of the wearer.

3. The throat microphone unit of claim 1, wherein the wireless transceiver and the at least one microphone are in electrical communication via at least one wire;
wherein the at least one wire comprises a flexible cable electrically connecting the microphone to the wireless transceiver; and
wherein the housing includes a main unit configured to house the wireless transceiver, a strip configured to house the flexible cable, and a sensor unit configured to house the microphone.

4. The throat microphone unit of claim 1, wherein the first microphone comprises a first MEMS microphone and the second microphone comprises a second MEMS microphone.

5. The throat microphone unit of claim 4, wherein the throat microphone unit includes a third microphone;
wherein the first MEMS microphone and the second MEMS microphone are positioned in the housing such that, when the throat microphone unit is worn, the first MEMS microphone and the second MEMS microphone point inward to a neck of the wearer; and
wherein the third microphone is positioned in the housing such that, when the throat microphone unit is worn, the third microphone and points upward to a mouth of the wearer.

6. The throat microphone unit of claim 1, further comprising a sensor configured for contact on at least a part of a throat of a person and configured to generate sensor data indicative of movement associated with speech generated by the person, wherein the sensor is configured to transmit the sensor data indicative of movement associated with speech generated by the person in order to determine whether to process the sound data generated by the least one microphone.

7. The throat microphone unit of claim 6, wherein the sensor comprises a vibration sensor that is in the housing with the at least one microphone.

8. A throat microphone system comprising:
a microphone unit configured to attach to a throat of a person, the microphone unit comprising a microphone configured to generate sound data and wireless communication functionality configured to transmit the sound data wirelessly;
a speaker;
a receiver unit configured to communicate via near-field communication and to drive the speaker; and
a mobile electronic device in communication with the receiver unit configured to:
receive the wirelessly transmitted sound data;
process the sound data by modifying the sound data in an audio range in order to generate processed sound data; and cause output or transmission of at least a part of the processed sound data to be output via the speaker by transmitting the at least a part of the processed sound data to the receiver unit in order for the receiver unit to drive the speaker with the at least a part of the processed sound data.

9. The throat microphone system of claim 8, wherein the mobile electronic device comprises a smartphone with communication functionality, the communication functionality configured to communicate with an external electronic device; and
wherein the smartphone is configured to cause the output or transmission of at least a part of the processed sound data by transmitting, using the communication functionality, the at least a part of the processed sound data to the external electronic device.

10. The throat microphone system of claim 9, wherein the communication functionality comprises Internet communication functionality;
wherein the external electronic device comprises a server; and
wherein the smartphone is configured to transmit the processed sound data to the server for at least one of storage or analysis.

11. The throat microphone system of claim 8, wherein the mobile electronic device is configured to process the sound data by:
analyzing at least one aspect of non-vocalized speech in the sound data;
responsive to analyzing the at least one aspect of the non-vocalized speech in the sound data, modify the sound data in order to vocalize the non-vocalized speech; and
causing the modified sound data to be output on a speaker in order to vocalize the non-vocalized speech.

12. The throat microphone system of claim 11, wherein the mobile electronic device is configured to analyze the at least one aspect of non-vocalized speech in the sound data by:
analyzing speech power spectrum data of the sound data.

13. The throat microphone system of claim 11, wherein the mobile electronic device is configured to determine whether there is non-vocalized speech in the sound data by:
analyzing the at least one aspect of non-vocalized speech in the sound data; and
analyzing data from at least one heart-rate sensor attached to the person.

14. The throat microphone system of claim 8, wherein the mobile electronic device comprises a smartphone.

15. A throat microphone system comprising:
a microphone unit configured to attach to a throat of a person, the microphone unit comprising a microphone configured to generate sound data and wireless communication functionality configured to transmit the sound data wirelessly; and
at least one electronic device, the at least one electronic device comprises a mobile electronic device with a memory, the memory configured to store a plurality of profiles, each of the plurality of profiles correlated to one or both of an aspect relating to a wearer of the microphone unit or environment in which the throat microphone system is used, each of the plurality of profiles including one or more parameters selected based on the aspect relating to the wearer or the environment in which the throat microphone system is used, the mobile electronic device configured to:
select a particular profile, from the plurality of profiles;
receive the wirelessly transmitted sound data;
process the sound data using the one or more parameters in the selected particular profile by modifying the sound data in an audio range in order to generate processed sound data; and
cause output or transmission of at least a part of the processed sound data.

16. The throat microphone system of claim 15, wherein the mobile electronic device comprises a smartphone.

17. The throat microphone system of claim 15, wherein the plurality of profiles comprise a first profile associated with a first disease and a second profile associated with a second disease; and
wherein the mobile electronic device is configured to select the particular profile from the first profile associated with the first disease and the second profile associated with the second disease based on a disease associated with the person.

18. The throat microphone system of claim 15, wherein the mobile electronic device is configured to select the particular profile based on an age associated with the person.

19. The throat microphone system of claim 15, wherein the mobile electronic device is configured to select the particular profile based on a nationality associated with the person.

20. A microphone unit comprising:
at least one housing;
a microphone at least partly in the at least one housing and configured for attachment on a throat of a person and configured to generate audio data;
a sensor at least partly in the at least one housing and configured for attachment on the throat of the person and to generate non-audio data; and
at least one processor in communication with microphone and the sensor, the at least one processor configured to:
analyze the non-audio data in order to determine whether the non-audio data is indicative that the person is generating speech;
responsive to determining that the non-audio data is indicative that the person is generating the speech, enable processing of the audio data by enabling filtering of the audio data, analog-to-digital conversion of the audio data, and signal processing of the audio data only responsive to determining that the non-audio data is indicative that the person is generating the speech; and
responsive to determining that the non-audio data is indicative that the person is not generating the speech, deactivating processing of the audio data.

21. The microphone unit of claim 20, wherein the sensor comprises an electromyography sensor configured to generate data indicative of movement of at least one muscle.

22. The microphone unit of claim 21, wherein the microphone unit and the electromyography sensor are within a same housing.

* * * * *